(12) United States Patent
Hatakeyama et al.

(10) Patent No.: US 10,085,612 B2
(45) Date of Patent: Oct. 2, 2018

(54) MANIPULATOR AND MANIPULATOR SYSTEM

(71) Applicant: OLYMPUS CORPORATION, Tokyo (JP)

(72) Inventors: Naoya Hatakeyama, Tokyo (JP); Takumi Isoda, Tokyo (JP); Masatoshi Iida, Tokyo (JP); Sadahiro Watanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 94 days.

(21) Appl. No.: 15/006,433

(22) Filed: Jan. 26, 2016

(65) Prior Publication Data

US 2016/0213224 A1 Jul. 28, 2016

Related U.S. Application Data

(63) Continuation of application No. PCT/JP2014/068687, filed on Jul. 14, 2014.

(30) Foreign Application Priority Data

Jul. 26, 2013 (JP) ................................. 2013-155481

(51) Int. Cl.
*A61B 1/005* (2006.01)
*A61B 1/00* (2006.01)
(Continued)

(52) U.S. Cl.
CPC .......... *A61B 1/00006* (2013.01); *A61B 1/008* (2013.01); *A61B 1/00045* (2013.01);
(Continued)

(58) Field of Classification Search
CPC ... A61B 1/0057; A61B 1/00045; A61B 1/018; A61B 1/04; A61B 1/06; A61B 1/0006; A61B 1/0052; B25J 3/04; B25J 9/1689
See application file for complete search history.

(56) References Cited

U.S. PATENT DOCUMENTS 6,565,554 B1 5/2003 Niemeyer
2004/0138530 A1 7/2004 Kawai et al.
(Continued)

FOREIGN PATENT DOCUMENTS

EP 1 776 057 B1 4/2007
EP 3 025 632 A1 6/2016
(Continued)

OTHER PUBLICATIONS

Extended Supplementary European Search Report dated Feb. 17, 2017 in related European Patent Application No. 14 82 9078.6.
(Continued)

*Primary Examiner* — Timothy J Neal
(74) *Attorney, Agent, or Firm* — Scully, Scott, Murphy & Presser, P.C.

(57) ABSTRACT

A manipulator and manipulator system in which a dynamic surplus is rapidly removed and a moving part actuates rapidly in association with the operation of an operating part. The manipulator includes an operating part operated by an operator, a moving part operated by the operating part, a transmitting part for coupling the operating part to the moving part to transmit driving force of the operating part to the moving part, a transmission compensating part for making up for a dynamic surplus occurring in the transmitting part in association with the operation of the operating part, an input part for acquiring a state of at least one of the operating, moving and transmitting part, and a control unit
(Continued)

for controlling the transmission compensating part depending on the state acquired by the input part.

12 Claims, 18 Drawing Sheets

(51) Int. Cl.

| | | |
|---|---|---|
| *B25J 3/04* | (2006.01) | |
| *B25J 9/16* | (2006.01) | |
| *A61B 90/96* | (2016.01) | |
| *A61B 90/98* | (2016.01) | |
| *A61B 1/008* | (2006.01) | |
| *A61B 1/018* | (2006.01) | |
| *A61B 1/04* | (2006.01) | |
| *A61B 1/06* | (2006.01) | |
| *A61B 1/31* | (2006.01) | |
| *A61B 34/00* | (2016.01) | |
| *A61B 34/30* | (2016.01) | |

(52) U.S. Cl.
CPC .......... *A61B 1/0052* (2013.01); *A61B 1/0055* (2013.01); *A61B 1/0057* (2013.01); *A61B 1/00105* (2013.01); *A61B 1/018* (2013.01); *A61B 1/04* (2013.01); *A61B 1/06* (2013.01); *A61B 1/31* (2013.01); *A61B 34/70* (2016.02); *A61B 34/71* (2016.02); *A61B 90/96* (2016.02); *A61B 90/98* (2016.02); *B25J 3/04* (2013.01); *B25J 9/1689* (2013.01); *A61B 2034/306* (2016.02); *A61B 2034/715* (2016.02); *G05B 2219/35417* (2013.01); *G05B 2219/39439* (2013.01); *G05B 2219/45118* (2013.01); *G05B 2219/49253* (2013.01)

(56) References Cited

U.S. PATENT DOCUMENTS

| | | | |
|---|---|---|---|
| 2005/0168571 A1 | 8/2005 | Lia et al. | |
| 2008/0262306 A1* | 10/2008 | Kawai | A61B 1/00039 600/118 |
| 2011/0295063 A1* | 12/2011 | Umemoto | A61B 1/008 600/109 |
| 2012/0046522 A1 | 2/2012 | Naito | |
| 2014/0094825 A1* | 4/2014 | Flaherty | A61B 19/2203 606/130 |

FOREIGN PATENT DOCUMENTS

| | | |
|---|---|---|
| JP | 2000-300511 A | 10/2000 |
| JP | 2005-013320 A | 1/2005 |
| JP | 2009-000179 A | 1/2009 |
| JP | 2009-195694 A | 9/2009 |
| JP | 2009-201607 A | 9/2009 |
| JP | 2011-019551 A | 2/2011 |
| WO | 2006/020943 A1 | 2/2006 |
| WO | WO 2011/108161 A1 | 9/2011 |

OTHER PUBLICATIONS

International Search Report dated Oct. 21, 2014 issued in PCT/JP2014/068687.

* cited by examiner

Angle of the distal end of the moving assembly in the lateral direction (°)

Amount of the dead zone

Handle angle in the lateral direction (°)

Amount of the dead zone (°)

○ Readings for the dead zone
— Fitting curve

Handle angle in the lateral direction (°)

FIG.16
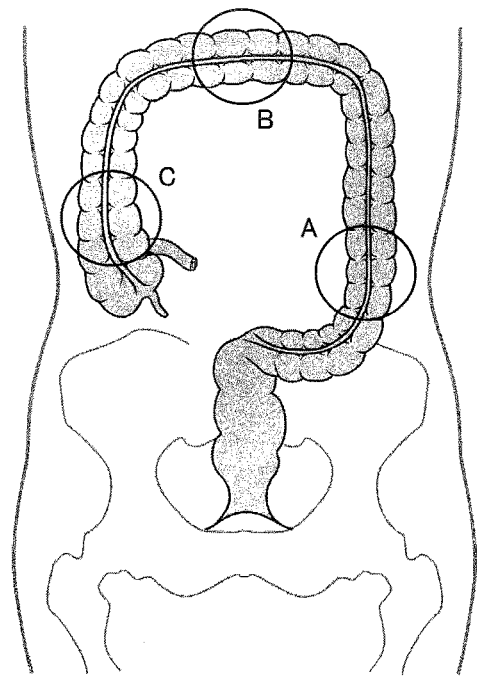
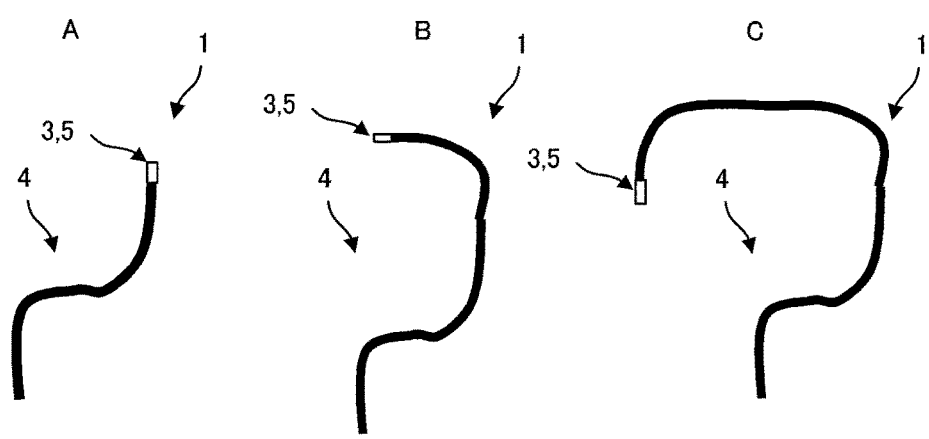
FIG.17A   FIG.17B   FIG.17C

MANIPULATOR AND MANIPULATOR SYSTEM

CROSS-REFERENCE TO RELATED APPLICATIONS

This application is a continuation claiming priority on the basis of Japan Patent Application No. 2013-155481 applied in Japan on Jul. 26, 2013 and based on PCT/JP2014/068687 filed on Jul. 14, 2014. The contents of both the PCT application and the Japan Application are incorporated herein by reference.

BACKGROUND OF THE INVENTION AND RELATED ART STATEMENT

The present invention relates to a manipulator and a manipulator system, each having an operating part mechanically connected to a moving part.

So far there has been a manipulator disclosed in JP(A) 2009-201607, wherein one end of a wire inserted through a hollow shaft is routed around a driving pulley and the other end is done around a driven pulley for power transmission.

With the manipulator disclosed in JP(A) 2009-201607, however, there is no power transmission ensured when no sufficient tension is applied to the wire routed around and between the driving pulley and the driven pulley. It is thus required to adjust the tension of the wire for rapid and precise power transmission.

FIGS. 22A-22c are illustrative in schematic of one conventional manipulator.

As shown in FIG. 22A, a wire 140 routed around and between an operating-side pulley 122 and a moving-side pulley 132 of a manipulator 110 in a neutral state has often a small slack 100. The manipulator of JP(A) 2009-201607 is previously cleared of such a small wire slack by adjustment of the wire tension.

On the other hand, such as when an operator (not shown) rotates a handle 121 from a neutral state of FIG. 22A in a direction indicated by an arrow A1, there are possible elongation of a wire 141 and friction or the like due to contact of a wire 140 with a guide member that receives the wire 140 in association with rotation of the handle 121 and operating-side pulley 122 in the direction indicated by the arrow A1, resulting in a dynamic slack 101 as shown in FIG. 22B.

Thereafter, when the handle 121 is reversed in a direction indicated by an arrow A2 as shown in FIGS. 22B and 22C, there is no tensile force transmitted to the moving-side pulley 132 until the dynamic slack 101 shown in FIG. 22B is taken out of the wire 140 with the result that the moving member 131 is unlikely to be actuated even with the operation of the handle 121 as shown in FIG. 22C.

The manipulator of JP(A) 2009-201607 does not clear such dynamic slack. Such a dynamic slack remains more or less even though that slack is previously cleared as is the case with such a manipulator as described in JP(A) 2009-201607. Even though the wire is previously cleared of any slack with the application of strong tension to it so as to prevent occurrence of any dynamic slack, another dynamic slack may not only occur from friction of the wire 140 with a wire guide member but also the wire may break off upon receipt of too strong a force.

A manipulator disclosed in U.S. Pat. No. 6,565,554 is designed to add a load determined by a friction compensation signal to an actuator for compensation thereby improving on operability. However, the manipulator described in U.S. Pat. No. 6,565,554 cannot gain control in association with state or performance fluctuations because compensation is made at a constant value.

With the problem in mind, it is an object of the invention to provide a manipulator and a manipulator system wherein any dynamic surplus is so rapidly removed that a moving part is rapidly actuated in association with the operation of an operating part.

SUMMARY OF THE INVENTION

A manipulator, comprising:
an operating part operated by an operator;
a moving part operated by the operating part;
a transmitting part that couples the operating part to the moving part to transmit rotation of the operating part to the moving part;
a transmission compensating part that makes up for a dynamic surplus occurring in the transmitting part in association with operation of the operating part;
an input part configured to acquire a state of at least one of the operating part, the moving part, and the transmitting part; and
a control unit configured to control the transmission compensating part depending on a state acquired by the input unit.

A manipulator system according to one embodiment of the invention comprises the manipulator, and a display unit for displaying images obtained through the manipulator, the manipulator includes an endoscope having a viewing optical system, an imaging device and a lighting optical system, and the control unit enables images obtained through the endoscope to be displayed on the display unit.

BRIEF EXPLANATION OF THE ACCOMPANYING DRAWINGS

FIG. 16 is a schematic view of the human large intestine.

FIGS. 17A-17C show the posture of the transmitting part upon insertion of the manipulator through the large intestine.

DETAILED DESCRIPTION OF EMBODIMENTS

One embodiment of the invention will now be explained.

Figure 1:
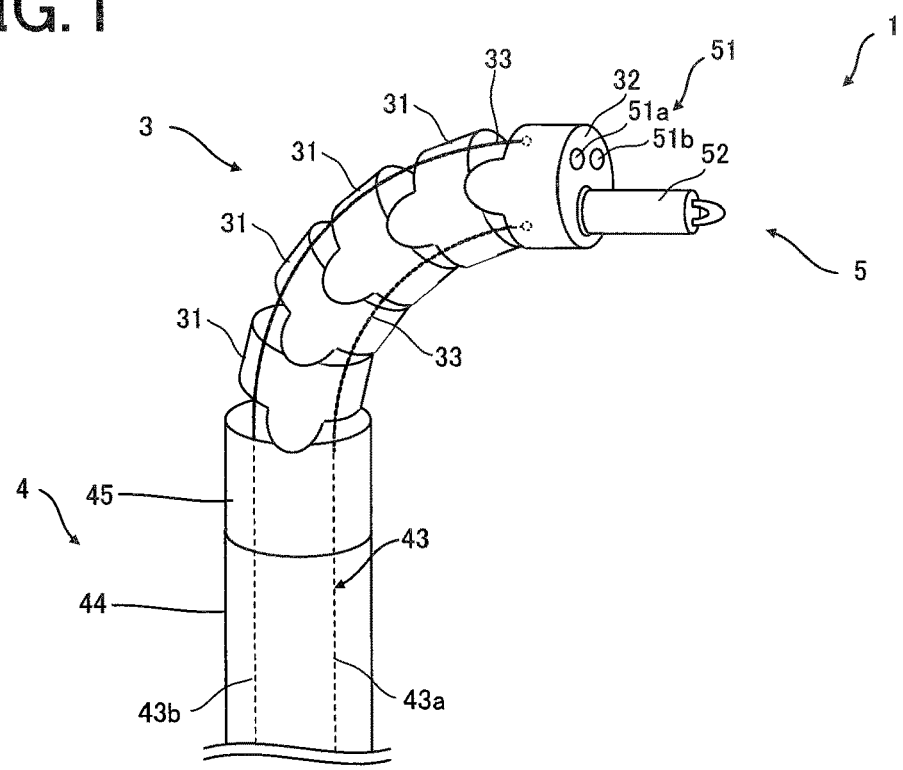
FIG. 1 shows one example of the manipulator according to the invention.
Figure 1:
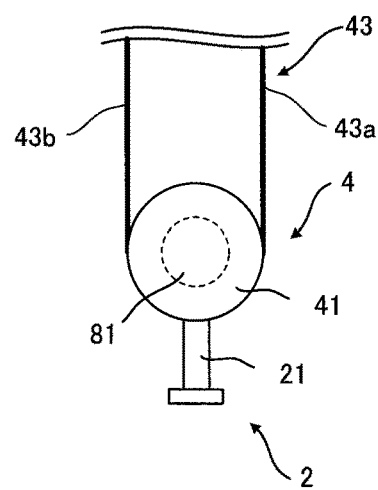

FIG. 1 shows on example of the manipulator 1 according to one embodiment of the invention.

As illustrated in FIG. 1, the manipulator 1 described here comprises an operating part 2, a moving part 3, a transmitting part 4, and a treatment part 5. The operating part 2 is mechanically connected to the moving part 3 through the transmitting part 4. As an operator operates the operating part 2 in action, it causes operating force to be transmitted to the moving part 3 via the transmitting part 4 for movement of the moving part 3.

The operating part 2 comprises a handle 21. In the embodiment described here, the handle 21 is schematically shown in the form of a rod member, but it may take the form of a multi-joint arm or a member having a shape suitable for operating a treatment part 5 or the like disposed on the moving part 3 such as the grips of scissors.

The moving part 3 includes a plurality of bendable blocks 31 and a rigid distal-end portion 32. The moving part 3 comprises a plurality of substantially ring-like bendable blocks 31 arranged axially side-by-side with the rigid distal-end portion 32 disposed at the distal end. The adjoining bendable blocks 31 are rotatable in relation to each other, and the bendable block 31 adjacent to the rigid distal-end portion 32 is rotatable too. The rigid distal-end portion 32 may optionally be provided with the treatment part 5.

The transmitting part 4 includes an operating-side pulley 41, a transmitting wire 43, a flexible portion 44, and a transition portion 45.

The operating-side pulley 41 is connected to the handle 21 in the operating part 2, and rotates based on the operation of the handle 21. The transmitting wire bundle 43 includes a first transmitting wire 43a and a second transmitting wire 43b fixed at the respective distal ends to the rigid distal-end portion 32 and at the respective other ends to the handle 21. As the rigid distal-end portion 32 moves on the basis of the operation of the handle 21, it causes movement of the moving part 3. The flexible portion 44 covers at least a part of the transmitting wire 43, and is formed of a bendable, flexible tubular member. The transition portion 45 is located on the side of the flexible portion 44 facing the moving part 3. The transition portion 45 is rotatably mounted with one end bendable block 31 of multiple bendable blocks 31 in the moving part 3. Note here that the transmitting part 4 may have a pulley on the moving part side.

The treatment part 5 includes an endoscope 51 and a treatment tool 52. The endoscope 51 includes a viewing optical system 51a, a lighting optical system 51b and so on. The endoscope 51 and treatment tool 52 are operated by the operating part 2 through a portion of the moving part 3 and transmitting part 4.

Through such a structure, the manipulator 1 described here is actuated as follows. As the operator first operates the handle 21 in the operating part 2, it causes the operating-side pulley 41 to rotate and a portion of the transmitting wire 43 routed around the operating-side pulley 41 to be towed thereby pulling one of the rigid distal-end portions 32 and slackening the other. As the rigid distal-end portion 32 is pulled, it causes the bendable blocks 31 to rotate, resulting in a bending of the moving part 3.

Figure 2A:
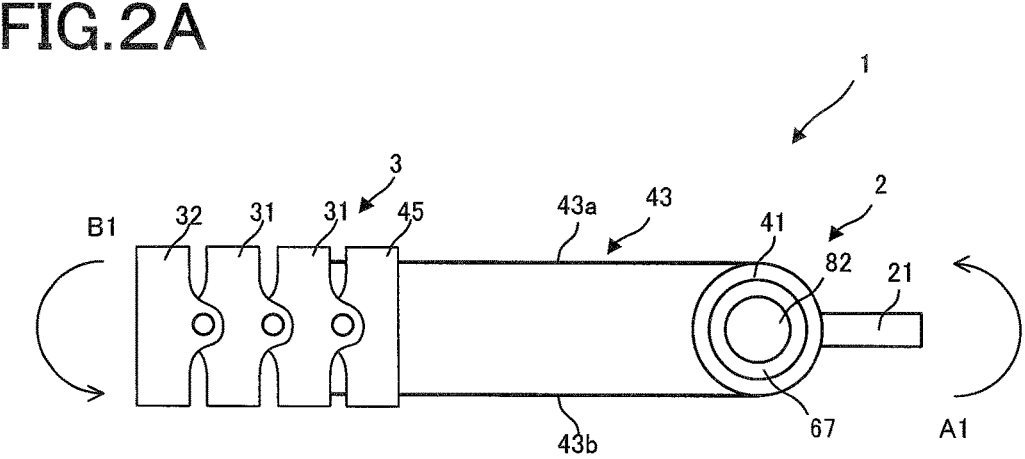
FIGS. 2A and 2B are illustrative in schematic of the manipulator according to the first embodiment of the invention.
Figure 2B:
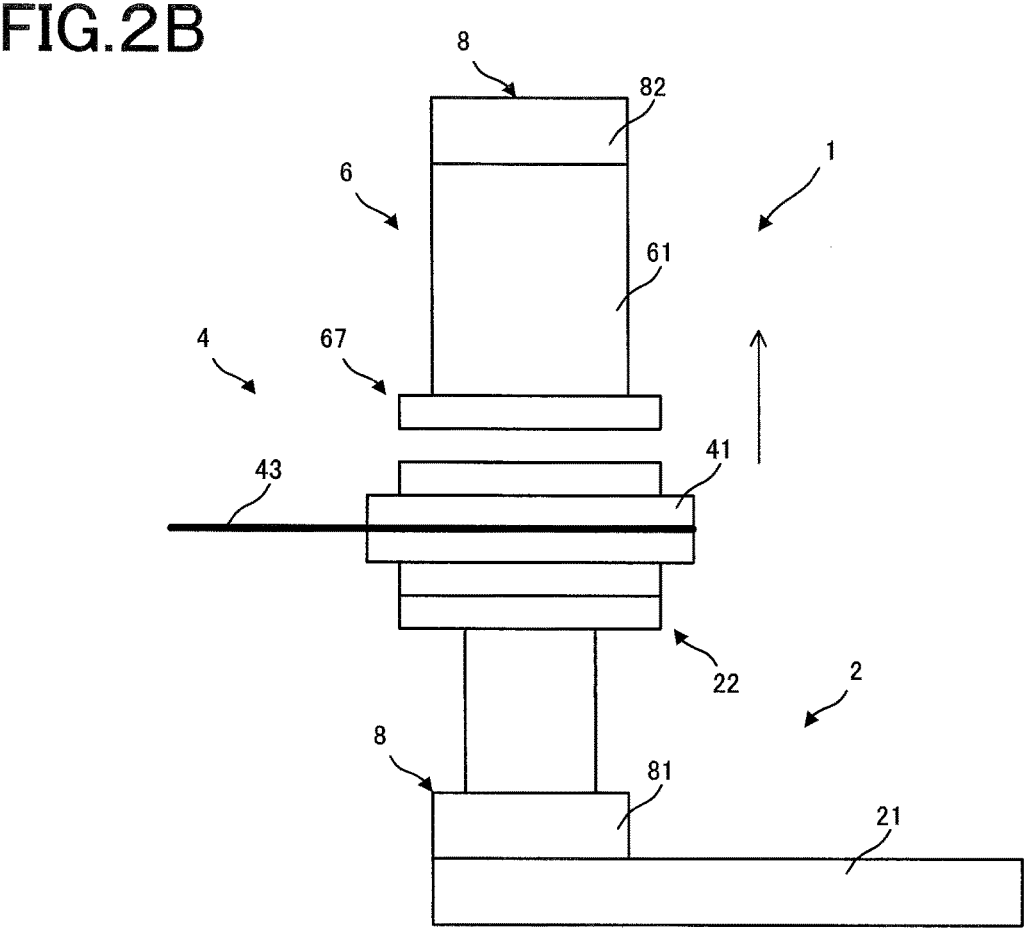

FIGS. 2A-2B are illustrative in schematic of the manipulator 1 according to the first embodiment of the invention.

The manipulator 1 according to the first embodiment of the invention comprises an operating part 2, a moving part 3, a transmitting part 4, a transmission compensating part 6, and an input part 8. The moving part 3 and transmitting part 4 may be constructed in the same way as explained with reference to FIG. 1.

The operating part 2 in the manipulator 1 shown in FIGS. 2A-2B includes a handle 21 and a first clutch 22, and the transmission compensating part 6 includes a compensating motor 61 and a second clutch 67. Further, the input part 8 includes a first encoder 81 and a second encoder 82.

The handle 21 forms an operating member while the first clutch 22 forms an operating-side disengagement member, and the compensating motor 61 forms a driving member while the second clutch 67 forms a driving-side disengagement member. Further, the first encoder 81 defines an operational state acquisition portion while the second encoder 82 defines a driving state acquisition portion.

It is here to be noted that the driving member is not limited to a motor; it may be any actuator capable of producing a driving force. Likewise the operational state acquisition portion is not limited to an encoder; any device capable of acquiring the rotational state of the operating part 2 may be used. For instance, use may be made of an angle sensor such as a potentiometer, an angular velocity sensor such as a tachogenerator, or any other device capable of acquiring the angle of rotation of the operating-side pulley 41. Likewise, the driving state acquisition portion is not limited to an encoder; any device capable of acquiring the rotational state of the compensating motor 61 may be used. For instance, use may be made of an angle sensor such as a potentiometer, or an angular velocity sensor such as a tachogenerator.

In the first embodiment described here, the handle 21 is schematically shown in the form of a rod-like member, but it may take the form of a multi-joint arm or a member having a shape suitable for operating a treatment tool or the like disposed on the moving part 3 such as the grips of scissors. The first clutch 22 is a member that is located between the handle 21 and the operating-side pulley 41 to cut off or disengage the transmission of force from the handle 21 to the operating-side pulley 41.

The compensating motor 61 rotates the operating-side pulley 41 for removal of a dynamic slack 101. The compensating motor 61 may also rotate the operating-side pulley 41 to assist in the rotation of the handle 21. The second clutch 67 is a member that is located between the compensating motor 61 and the operating-side pulley 41 to disengage the transmission of force from the compensating motor 61 to the operating-side pulley 41. Aside from the compensating motor 61, the operating part 2 may also be provided with an actuator for the purpose of assisting in it.

The first encoder 81 acquires the angle and direction of rotation of the handle 21 to convert them into a signal to be entered in the control unit, as will be described later, and the second encoder 82 acquires the angle and direction of rotation of the compensating motor 61 to convert them into a signal to be entered in the control unit, as will be described later. The first 81 and second encoder 82 produce a signal having a positive value in the case of one rotation and a signal having negative value in the opposite rotation.

Figure 3:
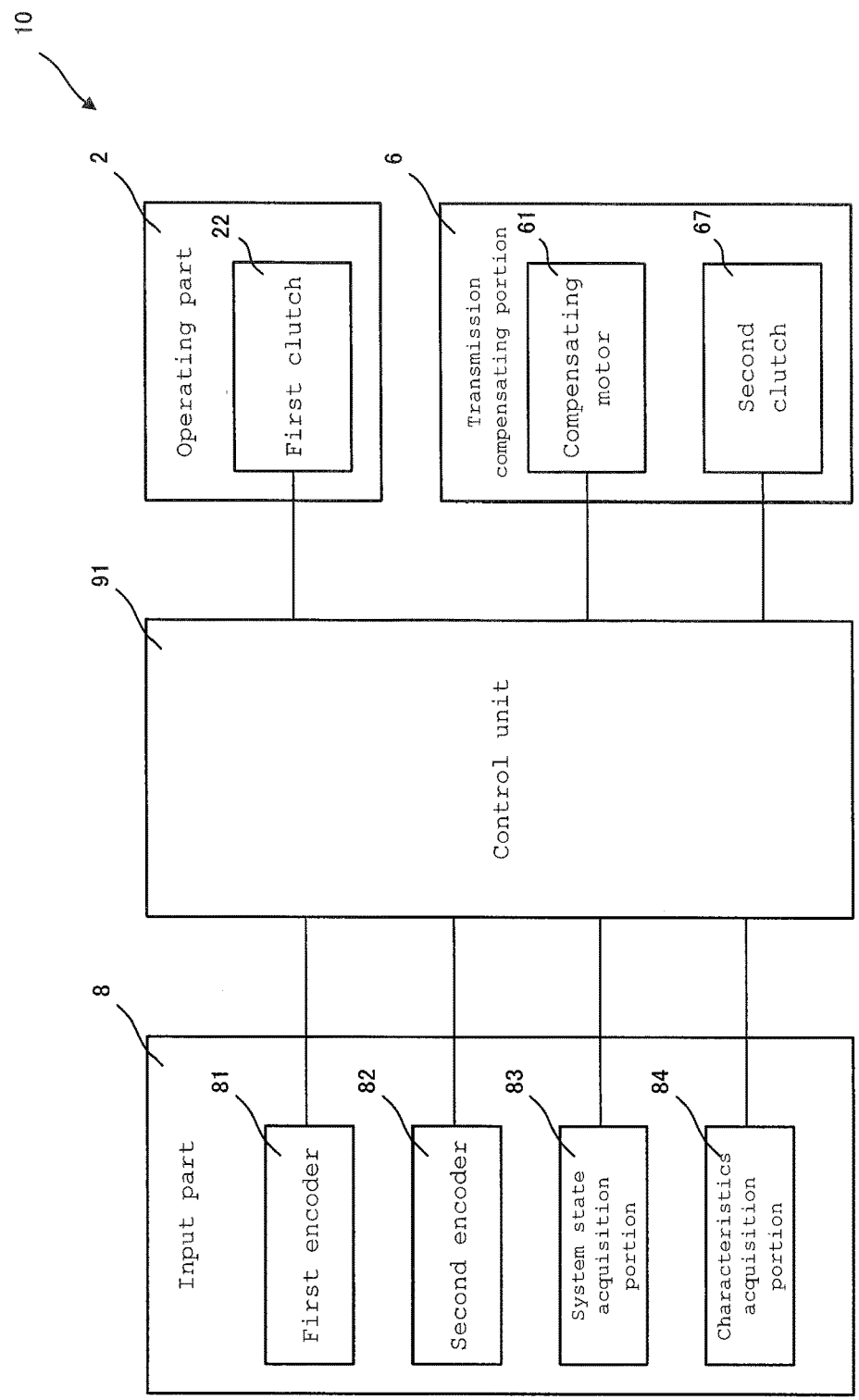
FIG. 3 is a block diagram for the manipulator according to the first embodiment of the invention.

FIG. 3 is a block diagram for the manipulator 1 according to the first embodiment of the invention.

In the manipulator 1 according to the first embodiment described here, the control unit 91 controls the first clutch 22 in the operating part 2 as well as the compensating motor 61 and second clutch 67 in the transmission compensating part 6 in response to the signals entered from the input part 8.

The input part 8 includes a first encoder 81 capable of detecting the angle and direction of rotation of the handle 21 shown in FIGS. 2A-2B, a second encoder 82 capable of detecting the angle and direction of rotation of the compensating motor 61, a system state acquisition portion 83 capable of detecting states of the moving part 3, transmitting part 4, treatment part 5 and so on, and a characteristics acquisition portion 84 capable of acquiring information about the geometry, material characteristics, etc. of the materials for forming the members used in the moving part 3, transmitting part 4, treatment part 5, etc.

For instance, the system state acquisition portion 83 may be designed to acquire the angles of the bendable blocks 31 shown in FIG. 1, the angle of rotation of the operating-side pulley 41, the tension of the transmitting wire 43 or the like. Input is preferably entered in the characteristics acquisition detector 84 by means of a model number selection button or the like. For instance, as the operator depresses down the model number button, it causes the parameters of the respective parts of the manipulator 1 already stored for each selected model number to be entered in the control unit 91.

How to control the manipulator 1 according to the first embodiment described here is now explained.

Figure 4:
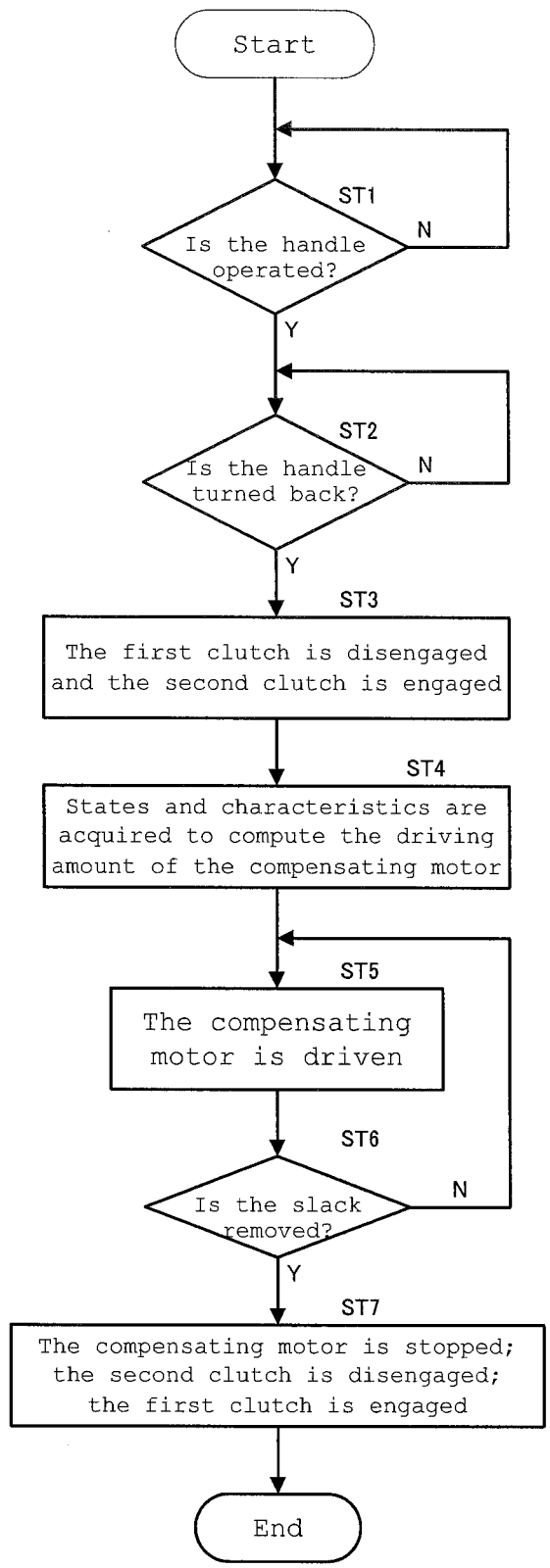
FIG. 4 is a control flowchart for the manipulator according to the first embodiment of the invention.

FIG. 4 is a control flowchart for the manipulator 1 according to the first embodiment of the invention. FIGS. 5A, 5B, 6A, 6B, 7A and 7B are illustrative in schematic of the actuation of the manipulator 1 according to the first embodiment of the invention.

First in Step 1, the control unit 91 determines whether or not the handle 21 is operated (ST1). Whether or not the handle 21 is operated in the operating part 2 is determined on the basis of an input from the first encoder 81.

Figure 5A:
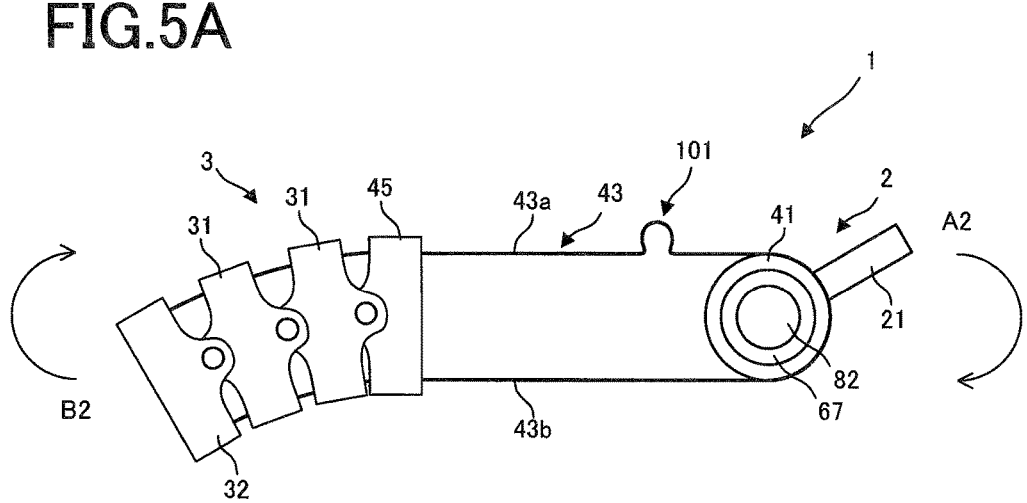
FIGS. 5A and 5B are illustrative in schematic of the actuation of the manipulator according to the first embodiment of the invention.
Figure 5B:
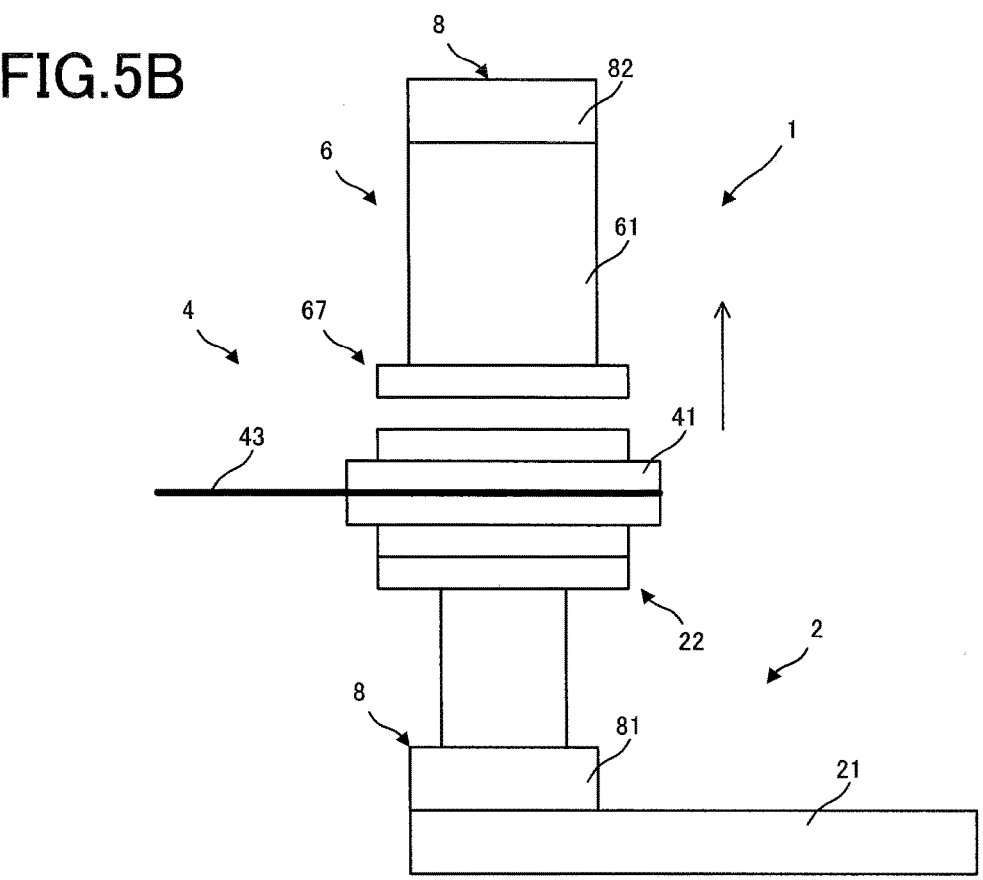

For instance, when the operator (not shown) rotates the handle 21 from a neutral state of FIGS. 2A-2B in a direction indicated by an arrow A1 to a state of FIGS. 5A-5B, there is a dynamic slack 101 occurring as shown in FIGS. 5A-5B, because of frictions, etc. resulting from mechanical actuation in association with the rotation of the handle 21 and operating-side pulley 41 in the direction indicated by arrow A1.

When the handle 21 is not operated in Step 1, the control processing goes back to Step 1. When the handle 21 is operated in Step 1, the control processing goes to Step 2 in which the control unit 91 determines whether or not the handle 21 is turned back (ST2). Whether or not the handle 21 is turned back is determined on the basis of the sign of an input from the first encoder 81.

When the handle 21 is not turned back in Step 2, the control processing goes back to Step 2. When the handle 21 is turned back in Step 2, the control processing goes to Step 3 in which the control unit 91 disengages the first clutch 22 and engages the second clutch 67 (ST3).

Figure 6A:
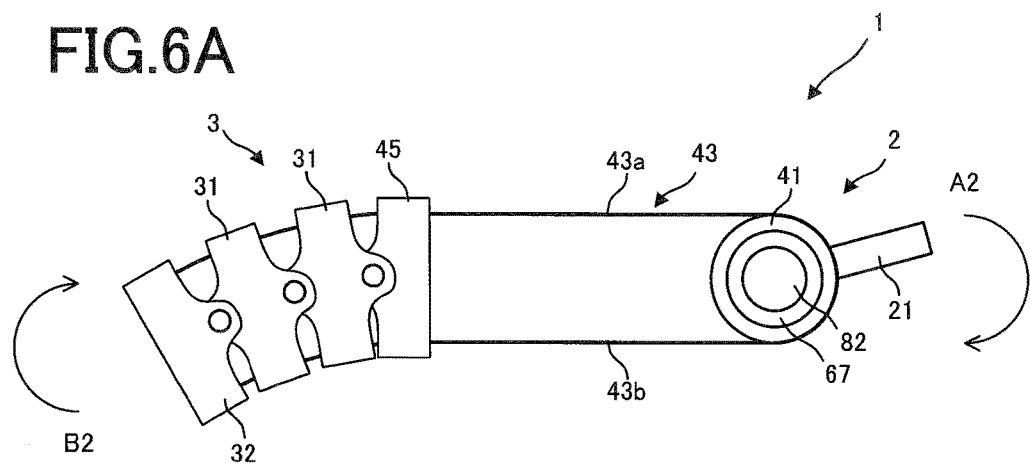
FIGS. 6A and 6B are illustrative in schematic of the actuation of the manipulator according to the first embodiment of the invention.
Figure 6B:
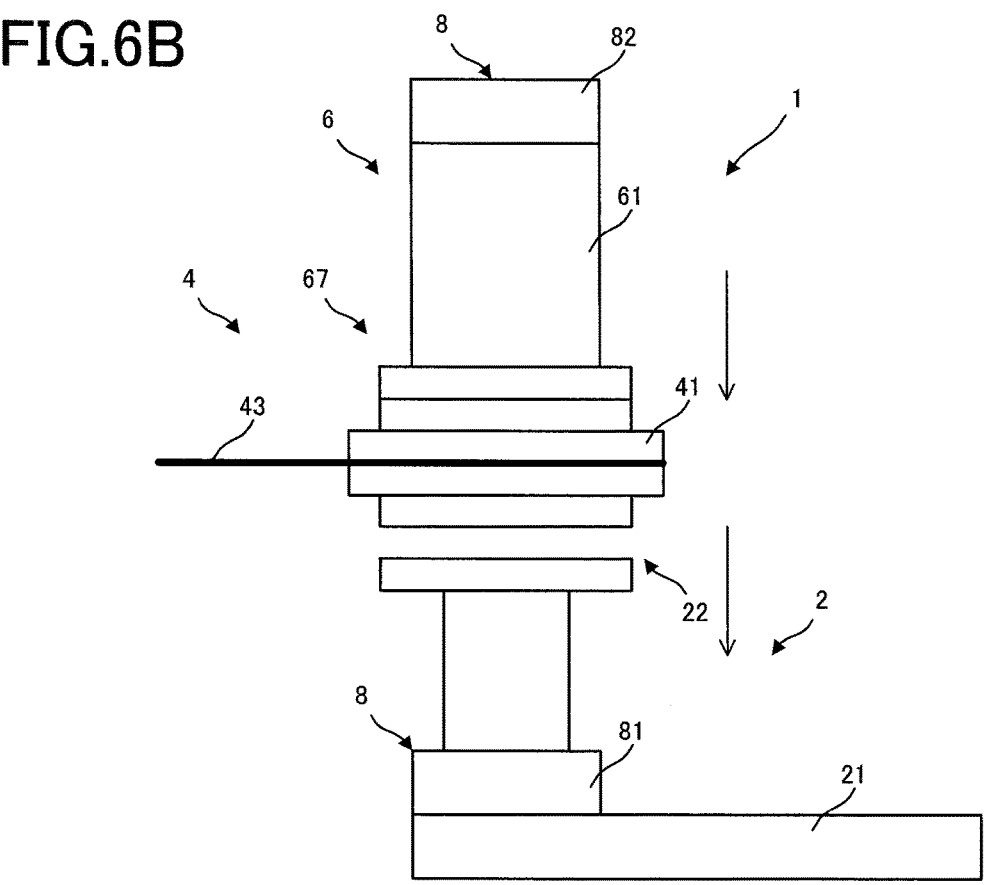

When the handle 21 is reversed in a direction indicated by an arrow A2 as shown typically in FIGS. 5A, 5B, 6A, 6B, 7A and 7B, the first encoder 81 detects the reversal of the handle 21. As the first encoder 81 detects the reversal of the handle 21, it causes the first clutch 22 in the operating part 2 to be disengaged and the second clutch 67 in the transmission compensating part 6 to be engaged as shown in FIGS. 6A-6B. Arrows in FIGS. 5A, 5B, 6A, 6B, 7A and 7B are indicative in schematic of clutch engagement/disengagement.

The control processing then goes to Step 4 in which the control unit 91 acquires the state and characteristics of the manipulator 1, and computes a driving amount of the compensating motor 61 (ST4).

The states of the manipulator 1 described here include the angles, angular velocities, displacements, tensions and so on of the operating part 2, moving part 3, transmitting part 4, treatment part 5, and compensating part 6 in such states shown typically in FIGS. 5A, 5B, 6A and 6B. Accordingly, the states of the manipulator 1 are acquired from the first encoder 81, second encoder 82 and system state acquisition portion 83, and the characteristics of the manipulator 1 are acquired from the characteristics acquisition portion 84 shown in FIG. 3.

Then, the control unit 91 computes the driving amount of the compensating motor 61 from the input values each acquired from the input part 8. In the embodiment described here, the following formula (1) is used as the computing formula.

$$u = f(\theta_{in}) \cdot \mathrm{sgn}(\theta'_{in}) \tag{1}$$

where u is an amount of compensation of the transmission compensating part, $\theta_{in}$ is a handle angle, $\theta'_{in}$ is a handle's angular velocity obtained by differentiation with respect to the handle angle, $f(\theta_{in})$ is a function indicative of the amount of compensation of the transmission compensating part relative to the handle angle, and $\mathrm{sgn}(\theta'_{in})$ is a sign corresponding to a shifting of the handle.

The control processing then goes to Step 5 in which the control unit 91 drives the compensating motor 61 (ST5).

As the compensating motor 61 is driven, it permits for rapid removal of the dynamic slack 101 in the first transmitting wire 43a, shown in FIGS. 5A-5B. Note here that in the state shown in FIGS. 6A-6B, even when the operating-side pulley 41 is rotated by the compensating motor 61, there is no transmission of the driving force of the compensating motor 61 to the handle 21, because the first clutch 22 is disengaged.

The control processing then goes to Step 6 in which the control unit 91 determines whether or not the dynamic slack 101 is removed (ST6). Determination of whether or not the dynamic slack 101 is removed is acquired from the first encoder 81, second encoder 82 and system state acquisition portion 83. For instance, the second encoder 82 connected to the motor determines it based on whether or not the amount of compensation of the transmission compensating part is reached.

When the dynamic slack 101 still remains in Step 6, the control processing goes back to Step 6. When the dynamic slack 101 is removed in Step 6, the control processing goes to Step 7 in which the compensating motor 61 is brought to a stop for disengagement of the second clutch 67 and engagement of the first clutch 22 (ST7).

Figure 7A:
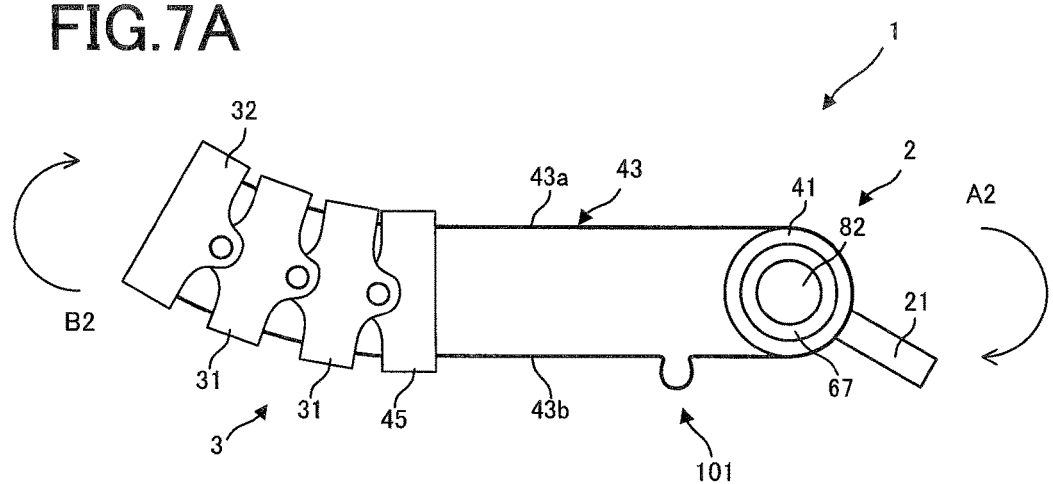
FIGS. 7A and 7B are illustrative in schematic of the actuation of the manipulator according to the first embodiment of the invention.
Figure 7B:
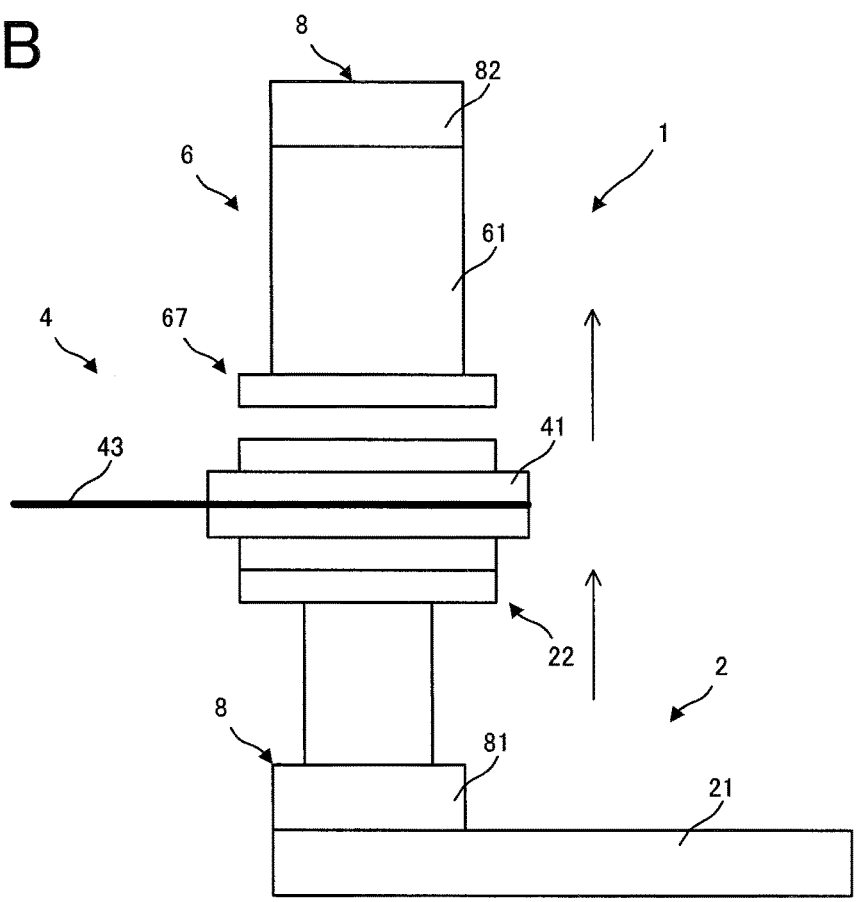

As the dynamic slack 101 is removed, it causes the first clutch 22 to be engaged, as shown in FIGS. 7A-7B, so that the moving part 3 rotates in a direction indicated by an arrow B2 under the tensile force of the transmitting wire 43 occurring from the rotation of the handle 21.

With the manipulator 1 according to the first embodiment of the invention, it is thus possible to achieve rapid removal of the dynamic slack 101 in the transmitting wire 43 and rapid rotation of the moving part 3 in association with the rotation of the handle 21.

The manipulator 1 according to the second embodiment of the invention is now explained.

Figure 8:
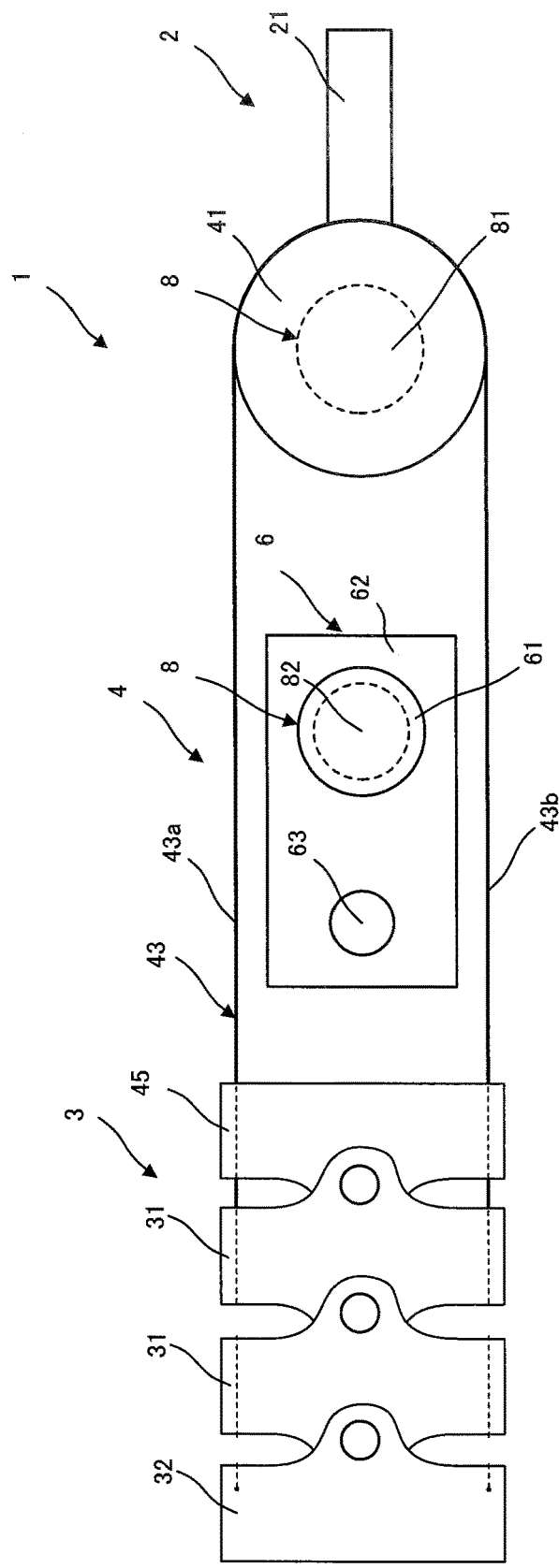
FIG. 8 is illustrative in schematic of the manipulator according to the second embodiment of the invention.

FIG. 8 is a schematic view of the manipulator 1 according to the second embodiment described here.

The manipulator of the second embodiment described here comprises an operating part 2, a moving part 3, a transmitting part 4, a transmission compensating part 6, and an input part 8. The operating part 2, moving part 3, transmitting part 4 and input part 8 may be the same in construction as described with reference to the first embodiment of the invention.

The transmission compensating part 6 includes a compensating motor 61, a moving member 62, and an urging member 63. The compensating motor 61 is provided to move the urging member 63. The urging member 63 is supported on the moving member 62, and rotates together with the moving member 62 to urge the transmitting wire 43 in the transmitting part 4.

Figure 9:
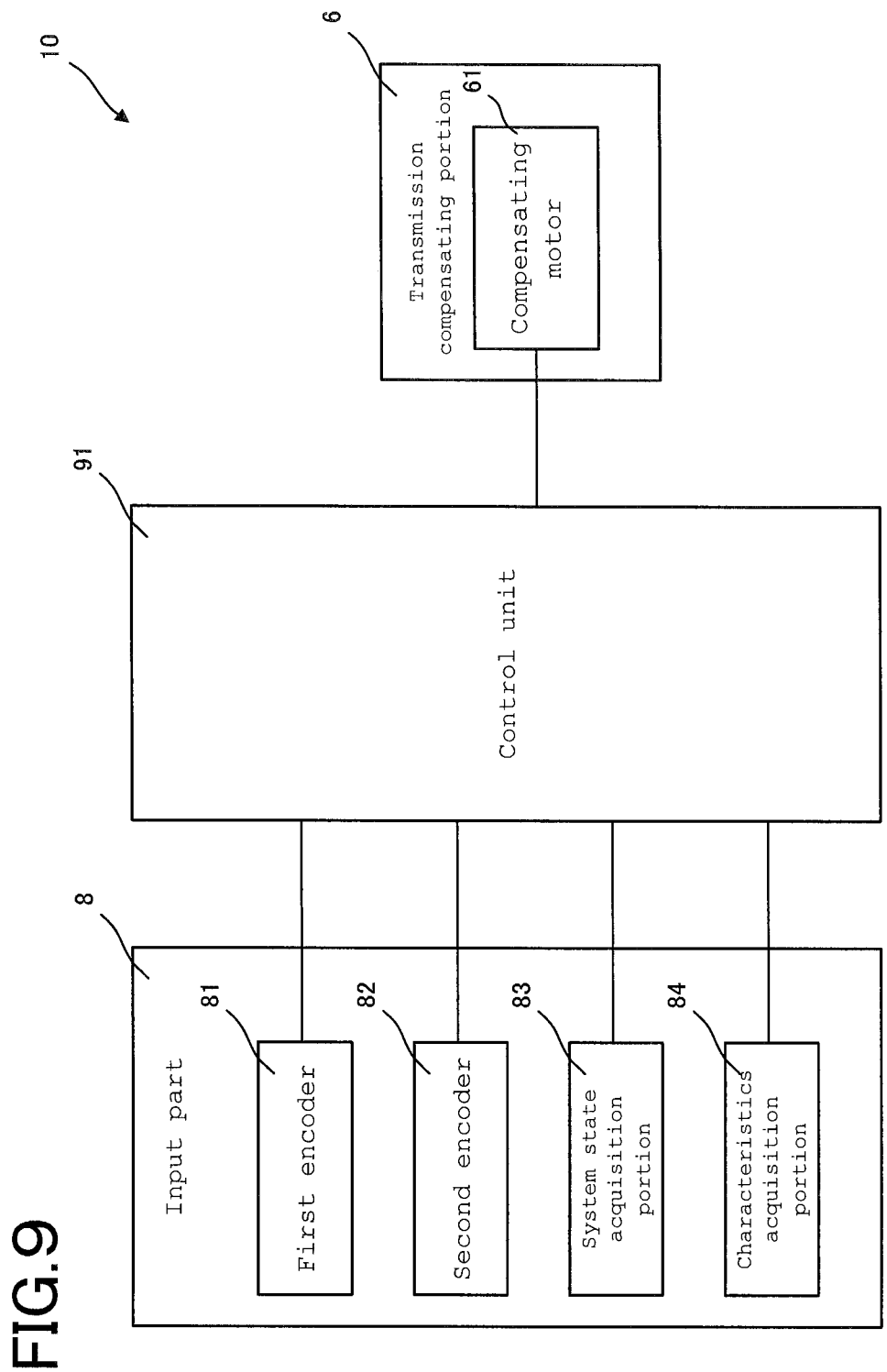
FIG. 9 is a block diagram for the manipulator according to the second embodiment of the invention.

FIG. 9 is a block diagram for the manipulator 1 according to the second embodiment.

In the manipulator 1 of the second embodiment, the control unit 91 controls the compensating motor 61 in the transmission compensating part 6 in response to a signal entered from the input part 8.

The input part 8 includes a first encoder 81 capable of detecting the angle and direction of rotation of the handle 21 shown in FIG. 8, a second encoder 82 capable of detecting the angle and direction of rotation of the compensating motor 61, a system state acquisition portion 83 capable of detecting states of the moving part 3, transmitting part 4, treatment part 5 and so on, and a characteristics acquisition portion 84 capable of acquiring information about the geometry, material characteristics, etc. of the materials for forming the members used in the moving part 3, transmitting part 4, treatment part 5, etc.

For instance, the system state acquisition portion 83 may be designed to acquire the angles of the bendable blocks 31 shown in FIG. 1, the angle of rotation of the operating-side pulley 41, the tension of the transmitting wire 43 or the like. Input is preferably entered in the characteristics acquisition portion 84 by means of a model number selection button or the like. For instance, as the operator depresses down the model number button, it causes the parameters of the respective parts of the manipulator 1 already stored for each selected model number to be entered in the control unit 91.

How to control the manipulator 1 according to the second embodiment described here is now explained.

Figure 10:
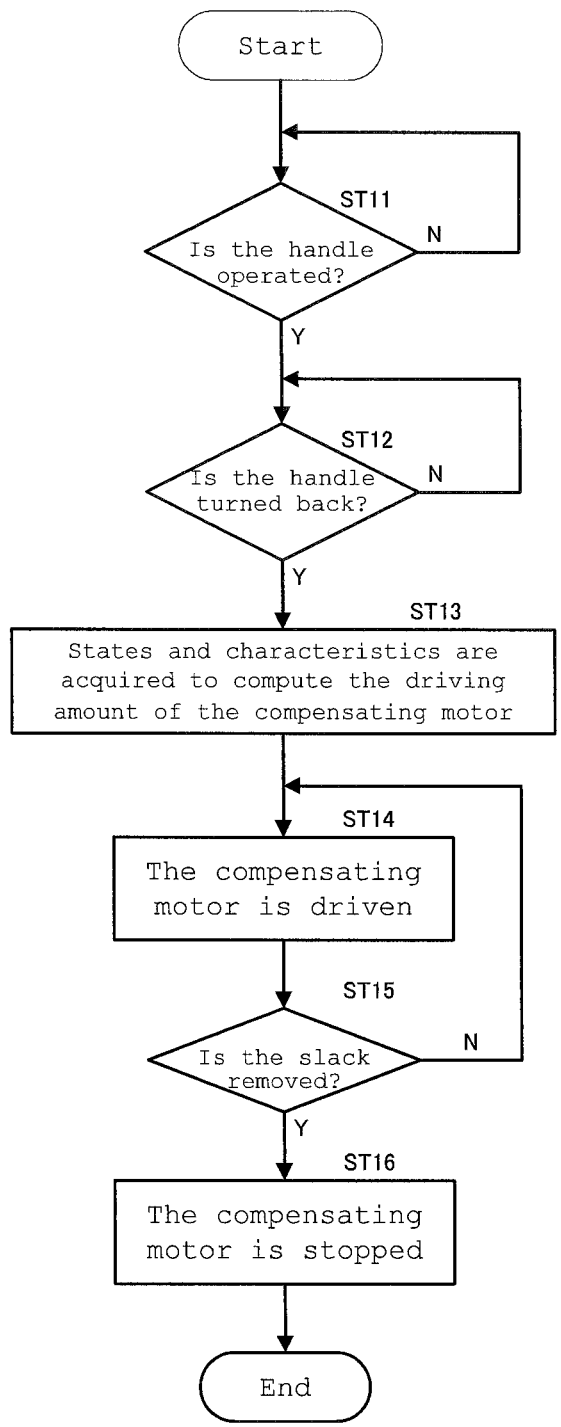
FIG. 10 is a control flowchart for the manipulator according to the second embodiment of the invention.

FIG. 10 is a control flowchart for the manipulator 1 according to the second embodiment of the invention, and FIGS. 11A-11D are illustrative in schematic of the actuation of the manipulator 1 according to the second embodiment of the invention.

First in Step 11, the control unit 91 determines whether or not the handle 21 is operated (ST11). Whether or not the handle 21 is operated in the operating part 2 is determined based on an input from the first encoder 81.

Figure 11A:
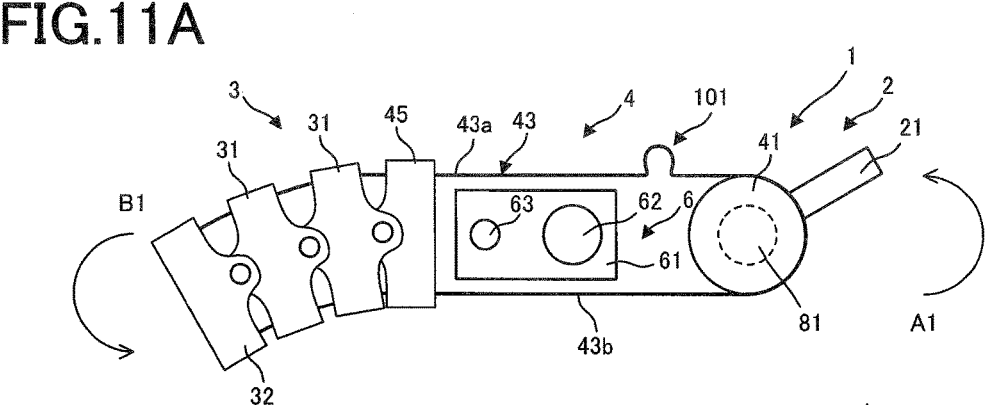
FIGS. 11A-11D are illustrative in schematic of the actuation of the manipulator according to the second embodiment of the invention.

For instance, when the operator (not shown) rotates the handle 21 from a neutral state of FIG. 8 in a direction indicated by an arrow A1 to a state of FIG. 11A, there is a dynamic slack 101 occurring in association with the rotation of the handle 21 and operating-side pulley 41 in a direction indicated by arrow A1, as shown in FIG. 11A.

When the handle 21 is not operated in Step 11, the control processing goes back to Step 11. When the handle 21 is operated in Step 11, the control processing goes to Step 12 in which the control unit 91 determines whether or not the handle 21 is turned back (ST12). Whether or not the handle 21 is turned back is determined based on the sign of an input from the first encoder 81.

When the handle 21 is not turned back in Step 12, the control processing goes back to Step 12. When the handle 21 is turned back in Step 12, the control processing goes to Step 13 in which the control unit 91 acquires the state and characteristics of the manipulator 1 to compute the driving amount of the compensating motor 61 (ST13).

Figure 11B:
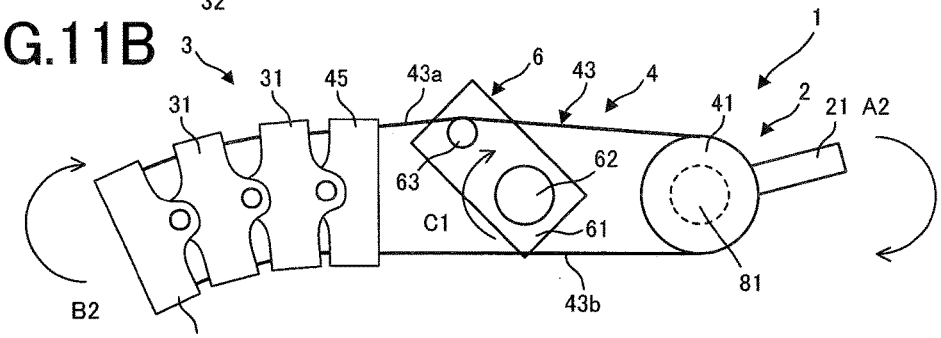

When the handle 21 is reversed in a direction indicated by an arrow A2 as shown typically in FIGS. 11A to 11B, the first encoder 81 detects the reversal of the handle 21. As the first encoder 81 detects the reversal of the handle 21, it causes the control unit 91 to acquire the state and characteristics of the manipulator 1 to compute the driving amount of the compensating motor 61.

The states of the manipulator 1 described here include the angles, angular velocities, displacements, tensions and so on of the operating part 2, moving part 3, transmitting part 4, treatment part 5 and compensating part 6 in such states shown typically in FIGS. 11A and 11B. Accordingly, the states of the manipulator 1 are acquired from the first encoder 81, second encoder 82 and system state acquisition portion 83 shown in FIG. 9, and the characteristics of the manipulator 1 are acquired from the characteristics acquisition portion 84 shown in FIG. 9.

Then, the control unit 91 computes the driving amount of the compensating motor 61 from the input values each acquired from the input part 8. In the embodiment described here, the following formula (1) is used as the computing formula.

$$u = f(\theta_{in}) \cdot \text{sgn}(\theta'_{in}) \tag{1}$$

where u is an amount of compensation of the transmission compensating part, $\theta_{in}$ is a handle angle, $\theta'_{in}$ is a handle's angular velocity obtained by differentiation with respect to the handle angle, $f(\theta_{in})$ is a function indicative of the amount of compensation of the transmission compensating part relative to the handle angle, and $\text{sgn}(\theta'_{in})$ is a sign corresponding to the shifting of the handle.

The control processing then goes to Step 14 in which the control unit 91 drives the compensating motor 61 (ST14). As the compensating motor 61 is driven, it causes the moving member 62 and urging member 63 to rotate in a direction indicated by an arrow C1, as shown in FIG. 11B.

In the manipulator 1 of the second embodiment described here, the urging member 63 rotates as shown in FIG. 11B, urging the first transmitting wire 43*a* in the transmitting part 4.

The control processing then goes to Step 15 in which the control unit 91 determines whether or not the dynamic slack 101 is removed (ST15). Determination of whether or not the dynamic slack 101 is removed is obtained from the first encoder 81, second encoder 82 and system state acquisition portion 83. For instance, the second encoder 82 may be used to determine whether or not there is a difference in the angle of rotation between the operating-side pulley 41 and moving-side pulley 42 or, alternatively, the tension of the transmitting wire 43, etc. may be used.

When the dynamic slack 101 still remains in Step 15, the control processing goes back to Step 15. When the dynamic slack 101 is removed in Step 15, the control processing goes to Step 16 in which the compensating motor 61 is brought to a halt (ST16).

Figure 11C:
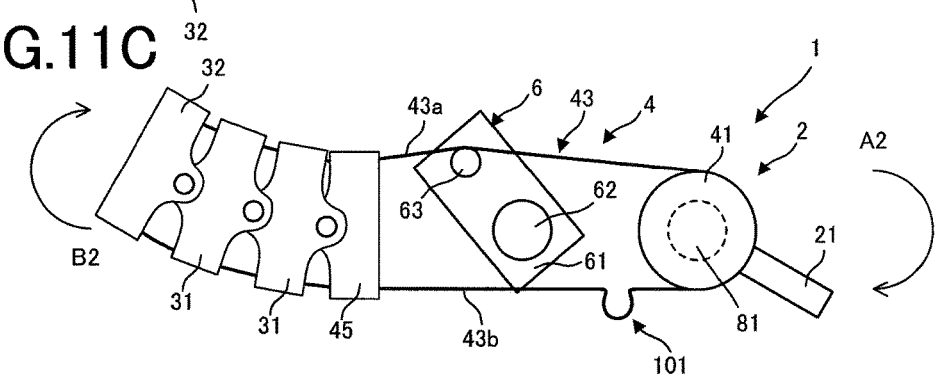

Removal of the dynamic slack 101 causes the moving part 3 to rotate in a direction indicated by an arrow B2 under the tensile force of the transmitting wire 43 occurring from the rotation of the handle 21, as shown in FIG. 11C.

With the manipulator 1 according to the second embodiment described here, it is thus possible to achieve rapid removal of the dynamic slack 101 in the transmitting wire 43 and rapid rotation of the moving part 3 in association with rotation of the handle 21.

It is here to be noted that as the handle 21 is rotated in a direction indicated by an arrow A2, it causes the dynamic slack 101 to occur in the transmitting wire 43 on the side to where the handle 21 rotates, as shown in FIG. 11C.

Figure 11D:
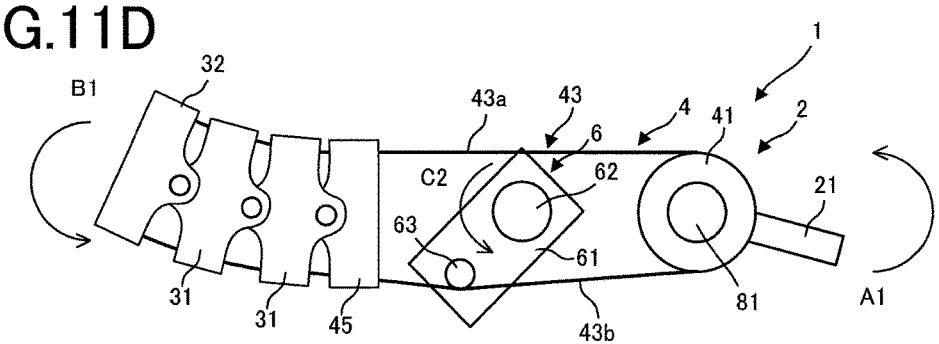

Thereafter, when the handle 21 is reversed from the direction indicated by arrow A2 to the direction indicated by arrow A1 as shown in FIGS. 11C and 11D, the first encoder 81 detects the reversal of the handle 21. As the first encoder 81 detects the reversal of the handle 21, it causes the compensating motor 61 in the transmission compensating part 6 to be driven so that, as shown in FIG. 11D, the moving member 62 and urging member 63 are rotated in a direction indicated by an arrow C2.

In the manipulator 1 according to the second embodiment described here, the urging member 63 rotates, as shown in FIG. 11D, urging the transmitting wire 43 in the transmitting part 4. As soon as the transmitting wire 43 is urged, the dynamic slack 101 in the transmitting wire 43, shown in FIG. 11C, is taken out. Removal of the dynamic slack 101 causes the moving part 3 to rotate in the direction indicated by arrow B1 under the tensile force of the transmitting wire 43 resulting from the rotation of the handle 21.

With the manipulator 1 according to the second embodiment described here, it is thus possible to achieve rapid removal of the dynamic slack 101 in the transmitting wire 43 and rapid rotation of the moving member 3 in association with the rotation of the handle 21.

Another example of the control processing of the control unit 91 according to the embodiment described here is now explained.

Figure 12:
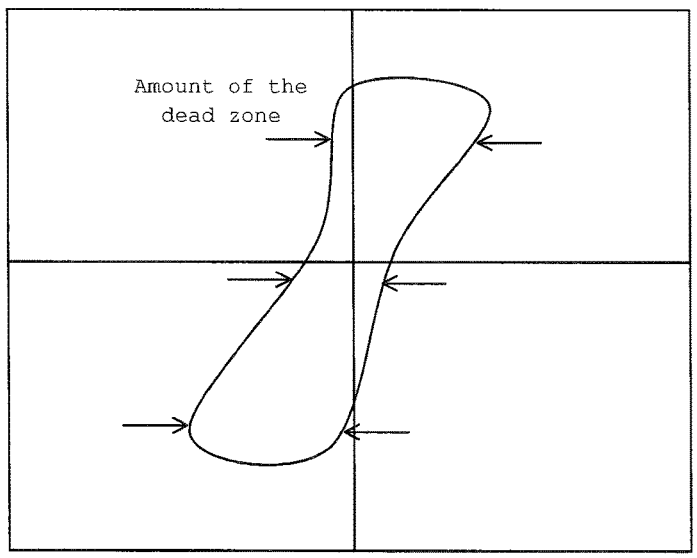
FIG. 12 is indicative of the angle of the distal end of the moving part in the lateral direction relative to the angle of the handle.
Figure 13:
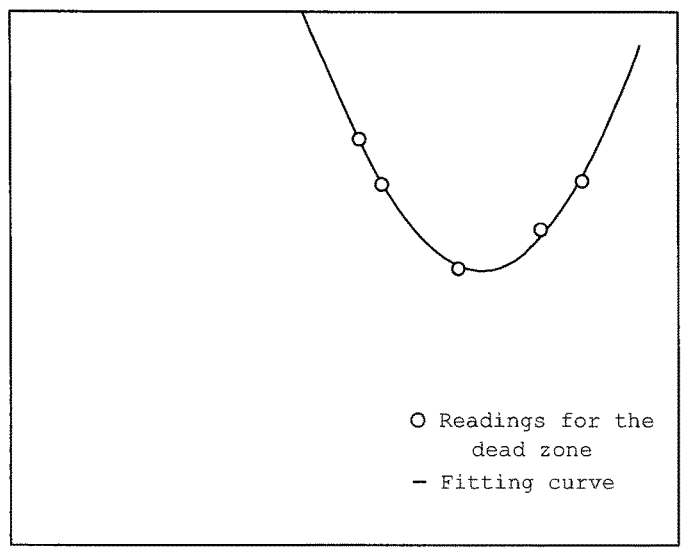
FIG. 13 is indicative of an amount of the dead zone relative to the angle of the handle.

FIG. 12 is indicative of the angle of the moving part relative to the handle angle, and FIG. 13 is indicative of an amount of a dead zone relative to the handle angle.

In the embodiment described here, the moving part 3 has a bendable structure, as shown in FIG. 1. The results of control may possibly vary between when the operating part 2 is operated while the moving part 3 extends straightforward and when the operating part 2 is operated while the moving part 3 bends laterally or vertically, because flexural rigidity changes under influences of a tube that covers the moving part 3, a tube that covers optical fibers or the treatment tool 5 inserted through the moving member 3, etc.

Therefore, the control unit 91 may control the transmission compensating part 6 depending on the bending state of the bendable blocks 31 shown in FIG. 1. For the bending state of the bendable blocks 31, the system state acquisition portion 83 may acquire the angle of the bendable blocks 31.

In the manipulator 1 according to the embodiment shown in FIG. 1, there is a change in the amount of a dead zone relative to the handle angle depending on the distal-end angle of the moving part 3 in the lateral or vertical direction, i.e., the direction of a center axis of a distal-end rigid portion 32. As shown typically in FIG. 12, the amount of the dead zone is more when the distal-end angle of the moving part 3 in the lateral direction is large than when that angle is small. In other words, the dynamic slack in association with the operation of the handle 21 grows larger when the moving part 3 is bent with a large bending of the distal end in the lateral direction than when the moving part 3 extends nearly straightforward.

Therefore, it is preferable that a lookup table or fitting formula is beforehand prepared from a graph indicative of the amount of the dead zone depending on the handle angle as shown in FIG. 13. When the driving amount of the compensating motor 61 is computed by the control unit 91 shown in FIG. 9, the prepared lookup table or the like is used to change the driving amount of the compensating motor 61 according to Formula 1 set such that the amount of the dead zone decreases depending on the distal end of the moving part 3 in the lateral direction.

Figure 14:
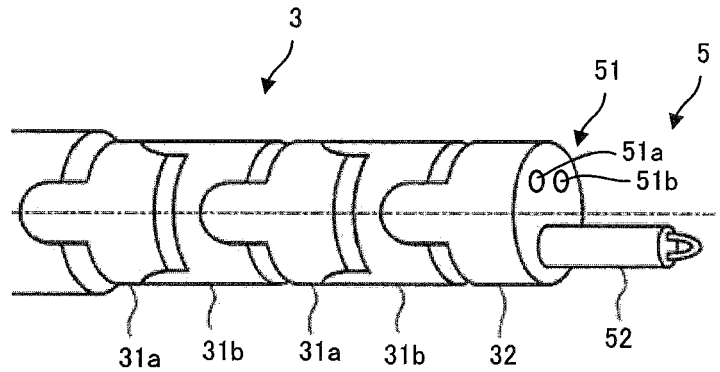
FIG. 14 is illustrative of a distal end portion of the manipulator according to another example of the invention.
Figure 15:
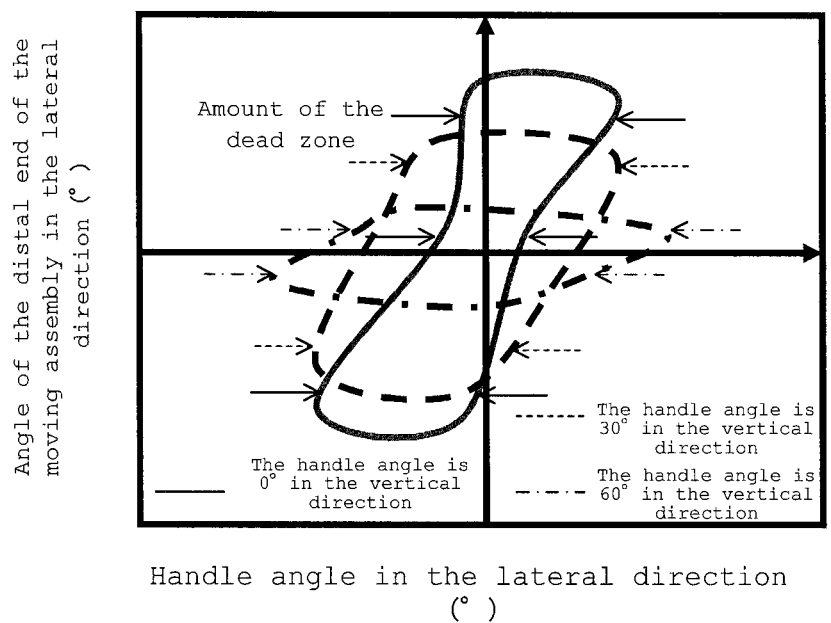
FIG. 15 is indicative of the angle of the handle and an amount of the dead zone relative to the angle of the distal end in the lateral direction in a state where the moving part is vertically bent.

FIG. 14 is illustrative of a distal-end portion of another example of the manipulator 1, and FIG. 15 is indicative of the angle of the handle 21, and the amount of the dead zone relative to the distal-end angle in the lateral direction while the moving part 3 is bent in the vertical direction.

As shown in FIG. 14, the bendable blocks 31 in the moving part 3 of the manipulator 1 may be mounted, each one rotated at an angle of 90° relative to the center axis, in such a way as to have two degrees of freedom in the vertical and lateral directions. When the moving part 3 is bendable at two degrees of freedom, the operating part 2 is operable at two degrees of freedom correspondingly. For the first encoder 81 for acquiring the operating state, use is preferably made of two encoders, one for rotation in the vertical direction and another for rotation in the lateral direction.

In this case, the following formula (2) is used as the computing formula for the driving amount of the compensating motor 61.

$$u_{LR}=(f(\theta_{LR})+f(\theta_{UD}))\cdot\text{sgn}(\theta'_{LR})$$

$$u_{UD}=(f(\theta_{LR})+f(\theta_{UD}))\cdot\text{sgn}(\theta'_{UD}) \quad (2)$$

where $u_{LR}$ is an amount of compensation of the transmission compensating part in the LR direction of the bending part, $u_{UD}$ is an amount of compensation of the transmission compensating part in the UD direction of the bending part, $\theta_{LR}$ is an angle of the handle in the LR direction, $(\theta'_{UD})$ is an angular velocity of the handle in the LR direction, $\theta_{UD}$ is an angle of the handle in the UD direction, $(\theta'_{UD})$ is an angular velocity of the handle in the UD direction, $f(\theta_{LR})$ is a function indicative of the amount of compensation of the transmission compensating part relative to the handle angle in the lateral direction; in the embodiment described here, $$f(\theta_{LR}) = a_1\theta^2_{LR} + a_2\theta_{LR} + a_3 \quad (2\text{-}1),$$

$f(\theta_{UD})$ is a function indicative of the amount of compensation of the transmission compensating part relative to the handle angle in the vertical direction; in the embodiment described here, $$f(\theta_{in}) = b_1\theta^2_{UD} + b_2\theta_{UD} + b_3 \quad (2\text{-}2),$$

and $\text{sgn}(\theta'_{in})$ is a sign corresponding to the shifting of the handle.

It is here to be noted that the driving amount of the compensating motor 61 may be figured from a lookup table or the like carrying predetermined driving amounts relative to angles in the vertical and lateral directions, and that the computing formula used may be in a polynomial or nonlinear form. For instance, coefficients may be varied as in the following formula (3).

$$f(\theta_{LR}, \theta_{LR}) = a_1\theta_{LR} \cdot b_1\theta_{uD}\theta^2_{LR} + a_2\theta_{LR} \cdot b_2\theta_{UD}\theta_{LR} + a_3\theta_{LR} \cdot b_3\theta_{UD} \quad (3)$$

It can be seen from FIG. 15 that when the handle 21 is operated while the moving part 3 shown in FIG. 14 is bent in the vertical direction, the amount of the dead zone grows larger than when the handle 21 is operated while the moving part 3 is vertically straightforward. The amount of the dead zone grows much larger upon operation of the handle 21 while the moving part 3 is bent in both the vertical direction and the lateral direction. In other words, the dynamic slack 101 in the transmitting wire 43 grows large in association with the operation of the handle 21 shown in FIG. 11A.

Therefore, it is preferable that a lookup table or the like is beforehand prepared from such a graph as shown in FIG. 15. When the driving amount of the compensating motor 61 is then computed by the control unit 91 shown in FIG. 9, the prepared lookup table or the like is used to change the driving amount of the compensating motor 61 such that the amount of the dead zone is eliminated depending on the distal-end angle of the moving part 3 in the vertical and lateral directions.

FIG. 16 is a schematic view of the human's large intestine, and FIGS. 17A-17C are indicative of the posture of the transmitting part 4 upon insertion of the manipulator 1 in the large intestine.

For the control unit 91 in the embodiment described here, it is preferable to change the driving amount of the compensating motor 61 depending on the posture of the transmitting member taken during use.

It can be seen from FIG. 16 that when the manipulator 1 according to the embodiment described here is used for treatment of an affected site in the large intestine, the position of the affected site to be treated in the large intestine differs from patient to patient. Accordingly, when a position A in the large intestine shown in FIG. 16 is treated, the transmitting part 4 takes such a posture as shown in FIG. 17A; when a position B in the large intestine shown in FIG. 16 is treated, the transmitting part 4 takes such a posture as shown in FIG. 17B; and when a position C in the large intestine shown in FIG. 16 is treated, the transmitting part 4 takes such a posture as shown in FIG. 17C.

The posture of the manipulator 1 in the large intestine may be acquired through an inserted endoscope posture detector or the like that serves as the system state acquisition portion 83. The inserted endoscope posture detector is used in combination with an inserted posture detection-dedicated endoscope having a built-in magnetic coil to receive magnetism generated from the magnetic coil at an antenna and present a real-time three-dimensional inserted posture display.

Before operation, the operator may obtain the position to be treated, etc. as preoperative information to predict the posture of the manipulator 1 having the system state acquisition portion 83 inserted through it. The operator may also obtain the length of the manipulator 1 inserted during operation as intra-operative information to predict the posture of the manipulator 1 having the system state acquisition portion 83 inserted through it. Note here that both preoperative information and intra-operative information may be used.

Alternatively, the transmitting part 4 in the manipulator 1 may be provided with a strain sensor and a bending sensor such as an optical fiber sensor as the system state acquisition portion 83 to detect the posture of the manipulator 1.

To recognize the posture of the manipulator 1, the embodiment described here is configured such that a preset posture parameter is acquired by the system state acquisition portion 83. A bending angle or bending radius may be used as the posture parameter. For instance, the transmitting part 4 may be sectioned to a plurality of intervals to find the bending angle, bending radius, bending length, etc. for each interval. The acquired posture parameter is entered in the control unit 91.

The computing formula for the control unit 91 may be defined as the following formula (4) wherein the amount of compensation for the posture is added to the amount of compensation for the operating part 2.

$$u_{LR} = (f(\theta_{LR}) + f(\theta_{UD})) \cdot \text{sgn}(\theta'_{LR})$$

$$u_{UD} = (f(\theta_{LR}) + f(\theta_{UD})) \cdot \text{sgn}(\theta'_{UD}) \quad (4)$$

where $u_{LR}$ is an amount of compensation of the transmission compensating part in the LR direction of the bending part, $u_{UD}$ is an amount of compensation of the transmission compensating part in the UD direction of the bending part, $\theta_{LR}$ is an angle of the handle in the LR direction, $(\theta'_{LR})$ is an angular velocity of the handle in the LR direction, $\theta_{UD}$ is an angle of the handle in the UD direction, $(\theta'_{UD})$ is an angular velocity of the handle in the UD direction, $\theta_{sh}$ is a posture parameter for the manipulator 1, $f(\theta_{LR})$ is a function indicative of the amount of compensation of the transmission compensating part relative to the handle angle in the lateral direction, $f(\theta_{sh})$ is a function indicative of the amount of compensation of the transmission compensating part relative to the handle angle in the vertical direction, $f(\theta_{sh})$ is a function indicative of the amount of compensation of the transmission compensating part for posture, and $\text{sgn}(\theta'_{in})$ is a sign corresponding to the shifting of the handle.

Such unerring acquisition of the posture of the transmitting part 4 makes more precise control feasible. Note here that it is preferable to acquire not only the posture of the transmitting part 4 but also the posture of the moving part 3.

It is here to be noted that a tension or position sensor for detection of the amount of slack in the transmitting wire 43 may be used as the system state acquisition detector 83. For instance, after the start of control by the transmission compensating part 6, compensation control is implemented until the tension of the transmitting wire 43 reaches a predetermined value or the transmitting wire 43 arrives at a predetermined position. When the position sensor is used, it is preferable to bias the transmitting wire 43 by a biasing member such that the transmitting wire 43 is located in a given position.

Figure 18:
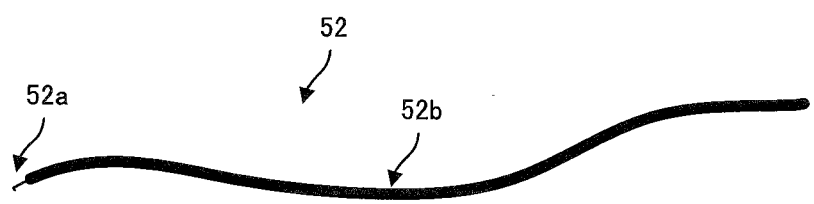
FIG. 18 is a schematic view of the treatment tool.
Figure 19:
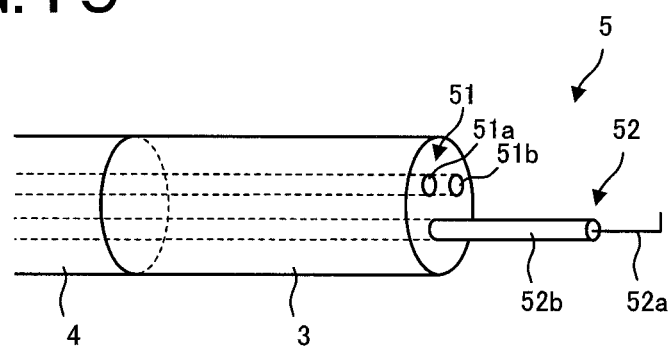
FIG. 19 is illustrative in schematic of the moving and transmitting assemblies on which the treatment part is mounted.
Figure 20:
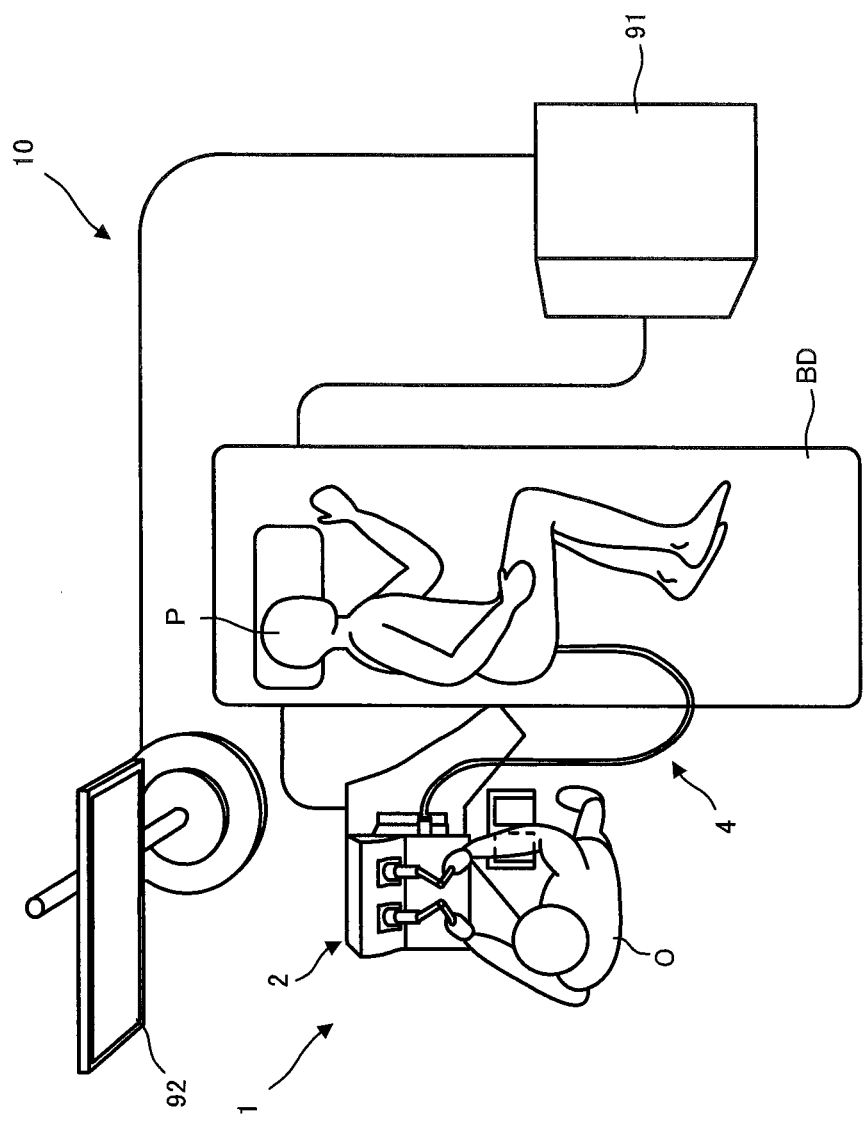
FIG. 20 shows a surgery support system to which the manipulator according to one embodiment of the invention is applied.
Figure 21:
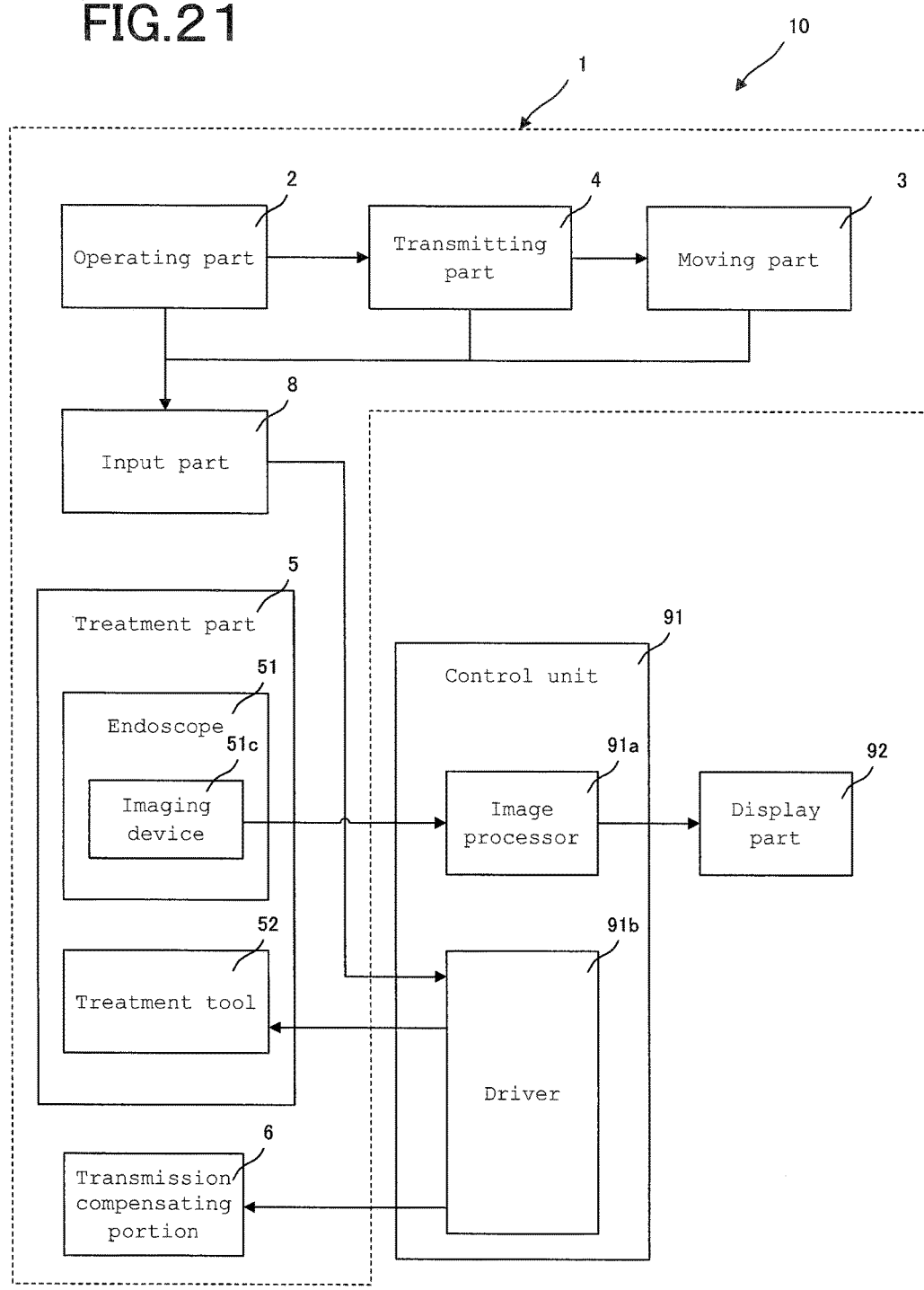
FIG. 21 is illustrative of the construction of a surgery support system to which the manipulator according to one embodiment of the invention is applied.
Figure 22A:
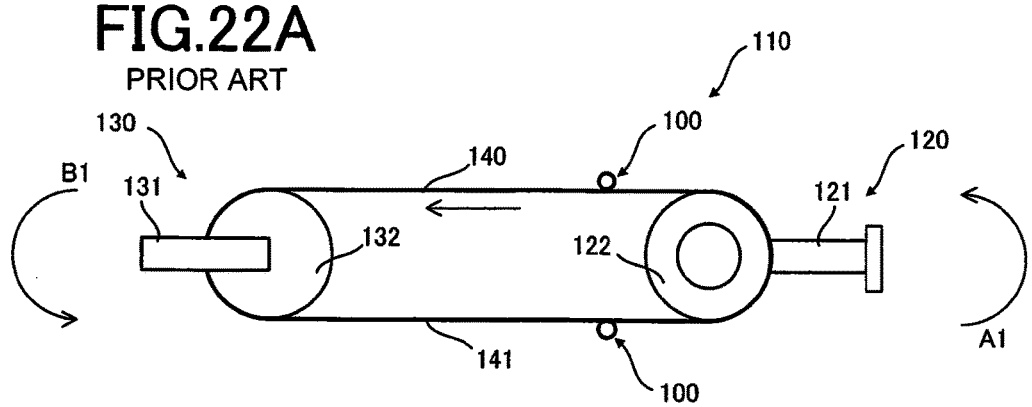
FIGS. 22A-22C are schematic views of the actuation of a prior art manipulator.
Figure 22B:
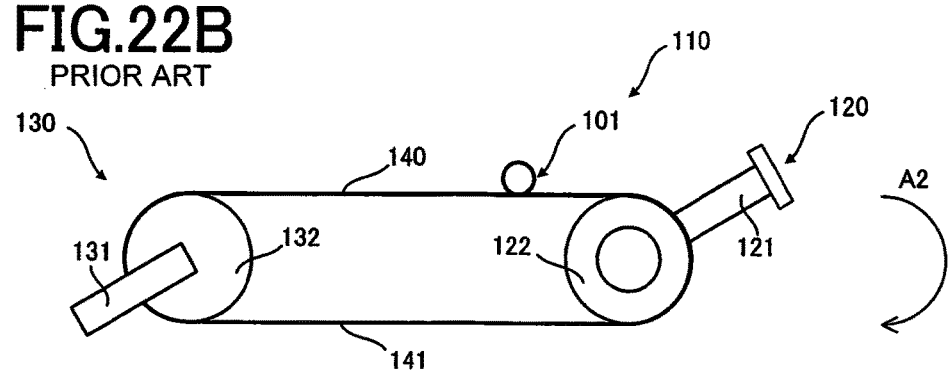
Figure 22C:
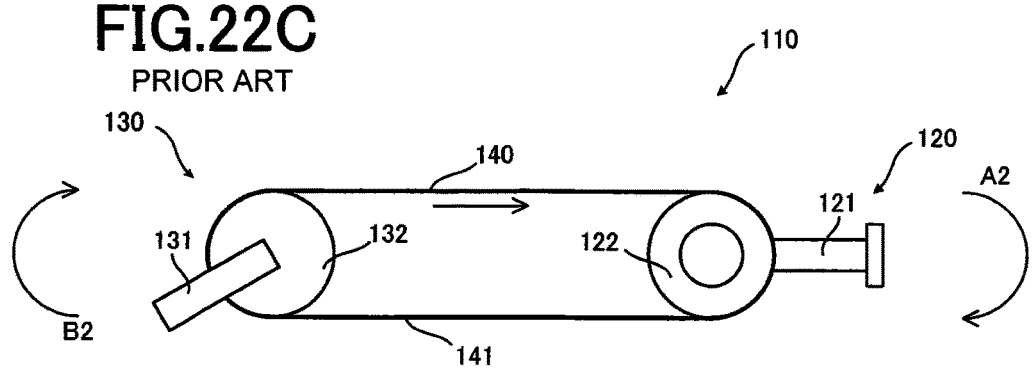

FIG. 18 is illustrative in schematic of the treatment tool 52, and FIG. 19 is illustrative in schematic of the moving part 3 and transmitting part 4 in which the treatment part 5 is installed. FIG. 20 is illustrative in schematic state of the treatment tool 52 before inserted through the flexible portion 44, and FIG. 21 is illustrative in schematic state of the treatment tool 52 after inserted through the flexible portion 44.

As shown in FIG. 18, the treatment tool 52 includes a distal end 52*a* and a tube 52*b*, and is inserted through the moving part 3 and transmitting part 4. This treatment tool 52 may be dismounted such as when only the endoscope 51 is used. Between when the treatment tool 52 is inserted through the moving part 3 and transmitting part 4 and when the treatment tool 52 is not, there are changes in the characteristics of the moving part 3 and transmitting part 4. For instance, the treatment tool 52 is less likely to bend when it is inserted through the moving part 3 and transmitting part 4 than when it is not.

For the control unit 91 in the embodiment described here, it is therefore preferable to change the driving amount of the compensating motor 61 depending on whether or not the treatment part 5 is inserted through the moving part 3 and transmitting part 4.

The treatment tool 52 is provided with a recording medium such as a barcode or IC tag. The recording medium is recorded with identification information capable of identifying the treatment tool 52 connected to it. A detector for identifying the treatment tool 52 is attached to each tool mount so that when a treatment tool 52 is attached to the tool mount, identification information about that treatment tool 52 is read out of the recording medium attached to it to send that identification information out to the control unit 91. The control unit 91 recognizes what sort of tool is inserted on the basis of the tool identification information received from the treatment tool identification portion.

The computing formula used in the control unit 91 may be expressed as the following formula (5) wherein the amount of compensation for the presence or absence of the treatment tool 52 is added to the amount of compensation for the operating part 2.

$$u=(f(\theta_{LR})+f(\theta_{UD})+\alpha)\cdot\text{sgn}(\theta'_{in}) \quad (5)$$

where u is an amount of compensation of the transmission compensating part, $f(\theta_{LR})$ is a function indicative of the amount of compensation of the transmission compensating part relative to the handle angle in the lateral direction, $f(\theta_{UD})$ is a function indicative of the amount of compensation of the transmission compensating part relative to the handle angle in the vertical direction, α is a parameter determined for each treatment tool (α is zero where there is no treatment tool), and $\text{sgn}(\theta'_{in})$ is a sign corresponding to the shifting of the handle.

Thus, the treatment tool 52 has a structure capable of attachment to or detachment from the moving part 3 and transmitting part 4, and the control unit 91 controls the transmission compensating part 6 depending on the presence or absence of the treatment tool 52 acquired by the characteristics acquisition portion 84, making sure more unerring control. Note here that the viewing optical system 51*a* and lighting optical system 51*b* of the endoscope 51 may also be controlled depending on whether it is or not.

Depending on how to treat a patient, the treatment tool 52 may be replaced with another tool. In this case, the whole of the treatment tool 52 including the distal-end portion 52*a* is replaced with another tool. After replacement, according to FIG. 19, another tool is again inserted through the moving part 3 and transmission part 4.

Note here that the viewing optical system 51*a* and lighting optical system 51*b* of the endoscope 51, too, are replaceable.

The treatment tools 52 may vary in flexural rigidity with sectional configuration and material type. For instance, a dual knife and an IT knife vary in terms of surface material, outer diameter, etc. and, hence, in terms of flexural rigidity and motion characteristics.

In the control unit 91 according to the embodiment described here, it is therefore preferable that the driving amount of the compensating motor 61 varies depending on the type of the treatment tool 52.

The type of the treatment tool 52 may be determined using an IC tag and a detector. For instance, a signal corresponding to the type of the treatment tool 52 may be prestored in the IC tag. Then, the detector mounted on the end of the flexible portion 44 or the like detects the IC tag attached to the treatment tool 52 to read the type of the treatment tool 52, and the IC tag sends the signal indicative of the type of the treatment tool 52 to the control unit 91.

A computing formula for the control unit 91 may be expressed by the following formula (6) wherein the amount of compensation for the type of the treatment tool 52 is added to the amount of compensation for the operating part 2.

$$u=(f(\theta_{LR})+f(\theta_{UD})+\alpha_A)\cdot\text{sgn}(\theta'_{in}) \quad (6)$$

where u is an amount of compensation of the transmission compensating part, $f(\theta_{LR})$ is a function indicative of the amount of compensation of the transmission compensating part 6 relative to the handle angle in the lateral direction, $f(\theta_{UD})$ is a function indicative of the amount of compensation of the transmission compensating part 6 relative to the handle angle in the vertical direction, $\alpha_A$ is a parameter determined for each treatment tool, and $\text{sgn}(\theta'_{in})$ is a sign corresponding to the shifting of the handle.

Thus, the treatment tool 52 has a structure capable of attachment to or detachment from the moving part 3 and transmitting part 4, and the control unit 91 controls the transmission compensating part 6 depending on the type of the treatment tool 52 acquired by the characteristics acquisition portion 84, making sure more unerring control. Note here that the viewing optical system 51*a* and lighting optical system 51*b* of the endoscope 51 may also be controlled depending on their type.

It is here to be noted that the characteristics acquisition portion 84 for recognizing the treatment tool 52 or the type of the treatment tool 52 may be configured such that the treatment tool is electrically or magnetically identified. For instance, the treatment tool may be provided with a magnet or resistance having characteristics varying with the treatment tool so that the characteristics of the magnet or resistance are detected by the characteristics acquisition portion. Alternatively, the treatment tool may be recognized through input means such as a keyboard, touch panel or button.

For the control unit 91 according to the embodiment described here, it is preferable to control the driving amount of the compensating motor 61 depending on the direction of operation of the operating handle 21. As shown typically in FIG. 1, the manipulator 1 according to the embodiment described here is not symmetrically formed with respect to the center axis of the rigid distal-end portion 32, resulting in a difference in motion characteristics depending on the direction of movement of the operating handle 21.

An associated compensation formula may then be determined depending on the left-to-right, right-to-left, bottom-to-top, and top-to-bottom shifting of the operating handle 21 to vary the driving amount of the compensating motor 61.

For the control unit 91 according to the embodiment described here, it is preferable to vary the driving amount of the compensating motor 61 depending on the velocity or acceleration upon a shifting of the operating handle 21.

The operating part 2 in the embodiment described here may also be provided with an actuator that weakens the tension of the transmitting wire 43 acting upon compensation for a slack in the transmitting wire 43.

Further, the input part 8 may be provided with a mode selection portion for selecting any one of a manual mode of hand-operating the handle 21, a compensation mode of actuating the transmission compensating part 6, and an assist mode of using the compensating motor 61 as an assist in the operation of the handle 21. Mode selection portion is preferably entered in by means of a mode selection button or the like. In particular, the input part 8 should preferably make an automatic transition to the manual mode at the time of emergencies such as a breakdown or power failure.

Next, a surgery support system 10 is explained as one example of the manipulator system to which the manipulator 1 described here is applied.

FIG. 20 shows the surgery support system 10 to which the manipulator 1 described here is applied, and FIG. 21 shows a typical system configuration of the surgery support system 10 to which the manipulator 1 described here is applied.

The manipulator 1 shown in FIG. 1 is applied to the surgery support system 10 described here. The surgery support system 10 comprises a manipulator 1, a control unit 91 for gaining control of the manipulator 1, and a display part 92 for displaying images obtained through the manipulator 1, wherein the manipulator 1 includes an operating part 2 operated by an operator O, a moving part 3 of FIG. 1 capable of being inserted through the body of a patient P on an operating table BD, for instance, a limp internal organ such as the large intestine, a transmitting part 4 for transmitting an input from the operating part 2 to the moving part 3 and capable of being partly inserted into the internal organ, and a treatment part 5 of FIG. 1 including an endoscope or the like attached to the distal end of the moving part 3.

As shown in FIG. 20, the operating part 2 includes a pair of operating handles attached to an operating table, and a footswitch or the like located on a floor surface. The operating part 2 may have a multi-joint structure. The operating part 2 is mechanically connected to the transmitting part 4 and moving part 3 to bend the moving part 3. The angle of the operating part 2 in action is acquired from an angle acquisition device such as an encoder, and the control unit 91 uses the acquired signals to actuate the treatment tool 52 and transmission compensating part 6 located at the distal end of the moving part 3 by way of a driver 91b.

In the rigid distal-end portion 32 of the moving part 3, the manipulator 1 includes an endoscope 51, a treatment tool 52 and so on in the form of the treatment part 5, as can be seen from FIG. 1. The endoscope 51 comprises a viewing optical system for obtaining in-vivo images, a lighting optical system 51b, an imaging device 51c and so on. An image obtained by the imaging device 51a via the viewing optical system 51c is sent out to an image processor 91a in the control unit 91. The image processed at the image processor 91a is displayed on the display unit 92. Then, the operator O operates the manipulator 1 while viewing the images displayed on the display unit 92.

According to such surgery support system 10, it is possible to display unerring images asked for by the operator.

The manipulator 1 according to the embodiment described here comprises the operating part 2 operated by the operator, the moving part 3 operated through the operating part 2, the transmitting part 4 that couples the operating part 2 to the moving part 3 to transmit rotation of the operating part 2 to the moving part 3, the transmission compensating part 6 for compensating a dynamic surplus occurring in the transmitting part 4 in association with the operation of the operating part 2, the input part 8 for acquiring a state of at least one of the operating part 2, moving part 3 and transmitting part 4, and the control unit 91 for controlling the transmission compensating part 6 depending on the state acquired by the input part 8. It is thus possible to remove the dynamic surplus rapidly and permit the moving part 3 to move rapidly in association with the actuation of the operating part.

In the manipulator 1 according to one embodiment of the invention, the input part 8 includes an operational state acquirement portion 81 for acquiring an operational state of the operating part 2, and the control unit 91 controls the transmission compensating part 6 depending on the operational state of the operating part 2 acquired by the operational state acquisition portion 81. It is thus possible to unerringly address a state of the operating part 2 thereby removing the dynamic surplus more rapidly and actuating the moving part 3 more rapidly.

In the manipulator according to one embodiment of the invention, the operational state acquisition portion 81 acquires a shifting direction of the operating part 2, and the control unit 91 controls the transmission compensating part 6 depending on the shifting direction of the operating part 2 acquired by the operational state acquisition portion 81. It is thus possible to actuate the moving part 3 unerringly.

In the manipulator 1 according to one embodiment of the invention, the operational state acquisition portion 81 acquires a velocity or acceleration upon a shifting of the operating part 2, and the control unit 91 controls the transmission compensating part 6 depending on the velocity or acceleration upon a shifting of the operating part 2 acquired by the operational state acquisition portion 81. It is thus possible to actuate the moving part 3 more unerringly.

In the manipulator 1 according to one embodiment of the invention, the input part 8 includes a system state acquisition portion 83 for acquiring a state of at least one of the moving part 3 and transmitting part 4, and the control unit 91 controls the transmission compensating part 6 depending on the state of at least one of the moving part 3 and transmitting part 4 acquired by the system state acquisition portion 83. It is thus possible to actuate the moving part 3 more unerringly.

In the manipulator 1 according to one embodiment of the invention, the input part 8 includes the system state acquisition portion 83 for acquiring a posture of at least one of the moving part 3 and transmitting part 4, and the control unit 91 controls the transmission compensating part 6 depending on the posture of at least one of the moving part 3 and transmitting part 4 acquired by the system state acquisition portion 83. It is thus possible to actuate the moving part 3 more unerringly.

In the manipulator 1 according to one embodiment of the invention, the moving part 3 includes a plurality of bendable blocks 31, the system state acquisition portion 83 acquires bending angles of a plurality of bendable blocks 31, and the control unit 91 controls the transmission compensating part depending on the bending angles of a plurality of bendable blocks 31 acquired by the system state acquisition portion 83. It is thus possible to actuate the moving part 3 more unerringly.

In the manipulator 1 according to one embodiment of the invention, the system state acquisition portion 83 acquires bending directions of a plurality of bendable blocks 31, and the control unit 91 controls the transmission compensating part 6 depending on the bending directions of a plurality of bendable blocks 31 acquired by the system state acquisition portion 83. It is thus possible to actuate the moving part 3 more unerringly.

In the manipulator 1 according to one embodiment of the invention, the input part 8 includes the characteristics acquisition portion 84 for acquiring characteristics of the moving part 3 and transmitting part 4, and the control unit 91 controls the transmission compensating part 6 depending on the characteristics of the moving part 3 and transmitting part 4 acquired by the characteristics acquisition portion 84. It is thus possible to actuate the moving part 3 more unerringly.

In the manipulator 1 according to one embodiment of the invention, the characteristics acquisition portion 84 acquires at least one of shapes and materials of the moving part 3 and transmitting part 4. It is thus possible to actuate the moving part 3 more unerringly.

The manipulator 1 according to one embodiment of the invention includes the treatment part 5 attachable to or detachable from the moving part 3 and transmitting part 4, the characteristics acquisition portion 84 determines the presence or absence of the treatment part 5, and the control unit 91 controls the transmission compensating part 6 depending on the presence or absence of the treatment part 5 determined by the characteristics acquisition portion 84. It is thus possible to actuate the moving part 3 more unerringly.

In the manipulator 1 according to one embodiment of the invention, the characteristics acquisition portion 84 acquires a type of the treatment part 5, and the control unit 91 controls the transmission compensating part 6 depending on the type of the treatment part 5 acquired by the characteristics acquisition portion 84. It is thus possible to actuate the moving part 3 more unerringly.

In the manipulator 1 according to one embodiment of the invention, the transmission compensating part 6 includes a driver member 61 for assisting in the operation of the operating part 2. It is thus possible to facilitate operation of the operating part 2.

In the manipulator 1 according to one embodiment of the invention, the control unit 91 is capable of a changeover between the compensation mode in which the transmission compensating part 6 is controlled, the assist mode in which the driver member 61 assists in operation of the operating part 2 and the manual mode in which the moving part 3 is operated by the operating part 2 alone.

It is thus possible to gain unerring control depending on situations.

With the manipulator system according to one embodiment of the invention comprising the manipulator 1 and the display unit 92 for displaying images obtained through the manipulator 1, wherein the manipulator 1 includes an endoscope having a viewing optical system, an imaging device and a lighting optical system, and the control unit 91 enables images obtained through the endoscope to be displayed on the display unit 92, it is possible to remove a dynamic surplus rapidly, actuate the moving part 3 rapidly in association with the operation of the operating part 2, and display unerring images asked for the operator.

It is to be understood that the invention is in no sense limited to the embodiments described herein. Explanations of the embodiments include a number of exemplary specifics; however, it would be obvious to those skilled in the art that variations or modifications added to them are encompassed in the scope of the invention. Thus, exemplary embodiments of the invention are herein disclosed without ridding the claimed invention of any generality and imposing any limitation thereon.

EXPLANATIONS OF THE REFERENCE NUMERALS

1: Manipulator
2: Operating part
21: Handle (Operating member)
22: First clutch (Operating-side disengagement member)
3: Moving part
31: Bendable blocks
32: Rigid distal-end portion
33: Moving wire
4: Transmitting part
41: Operating-side pulley
43: Transmitting wire
44: Flexible portion
45: Transition portion
5: Treatment part
51: Endoscope
52: Treatment tool
6: Transmission compensating part
61: Compensating motor (driver member)
62: Moving member
63: Urging member
66: Compensating motor (driver member)
67: Second clutch (Driving-side disengagement member)
8: Input part
81: First encoder (operating state acquisition portion)
82: Second encoder (driving state acquisition portion)
83: System state acquisition portion
84: Characteristics acquisition portion
10: Surgery support system
91: Control unit
92: Display unit

What is claimed is:

1. A manipulator including a distal end and a proximal end, the manipulator comprising:
an operating part located at the proximal end and operated by an operator;
a moving part located at the distal end and made movable operated by the operating part;
an operating part-side pulley located at the operating part to drive the moving part by way of a wire associated with rotational operation of the operating part;
a motor adapted to rotate the operating part-side pulley; and
a controller comprising hardware, the controller being configured to control the motor,
wherein when the operating part is rotated in a first direction whereby the operating part is changed from a state where the moving part is bent into a second direction that is a reverse direction relative to the first direction, the operating part-side pulley is disengaged from the operating part to connect the operating part-side pulley to the motor so that the operating part-side pulley is rotated to pull the wire.

2. A manipulator according to claim 1, wherein the controller controls rotation of the operating part-side pulley connected to the motor in association with a direction of rotation of a first encoder provided at the operating part to detect a direction or angle of rotation of the operating part-side pulley.

3. A manipulator according to claim 1, wherein the controller controls rotation of the motor and the operating part-side pulley in association with a speed or acceleration of rotation of the operating part.

4. A manipulator according to claim 1, wherein the controller controls the motor based on information about at least one of the moving part and the operating part-side pulley.

5. A manipulator according to claim 4, wherein the controller controls the motor based on a posture of at least one of the moving part and the operating part-side pulley.

6. A manipulator according to claim 4 or 5, wherein the moving part includes a plurality of bendable blocks, and a first encoder provided at the operating part to detect a direction or angle of rotation of the operating part-side pulley or a second encoder provided at the motor to detect a direction or angle of rotation of the motor to acquire information about angles of bending the plurality of bendable blocks, allowing the controller to control the motor depending on angles of rotation of the plurality of bendable blocks.

7. A manipulator according to claim 6, wherein the controller controls the motor depending on angles of bending of the plurality of bendable blocks.

8. A manipulator system, comprising:
a manipulator as recited in claim 1; and
a display for displaying images obtained through the manipulator;
wherein the manipulator includes an endoscope having a viewing optical system, an imaging sensor and a lighting optical system, and the controller enables images obtained through the endoscope to be displayed on the display.

9. A manipulator according to claim 1, wherein the operating part-side pulley is interposed between the operating part and the motor.

10. A manipulator according to claim 1, wherein when the operating part is rotationally operated in the first direction upon bending of the moving part, the controller gains control such that a slack in the wire disposed between the operating part-side pulley and the moving part is removed upon changing of the operating part from the first direction into the second direction.

11. A manipulator according to claim 1, wherein after connection of the operating part-side pulley to the motor, the operating part-side pulley is disengaged from the motor and connected to the operating part.

12. A manipulator including a distal end and a proximal end, comprising:
an operating part located at the proximal end and operated by an operator;
a moving part located at the distal end and made movable by the operating part;
an operating part-side pulley located at the operating part to drive the moving part by way of a wire associated with rotational operation of the operating part;
a motor adapted to rotate the operating part-side pulley;
a controller comprising hardware, the controller being configured to control the motor,
a first clutch located at the operating part to be capable of being disengaged from the operating part-side pulley;
a second clutch located on the motor side to be capable of being disengaged from the operating part-side pulley;
a first encoder located at the operating part to detect a direction of rotation of the operating part; and
a second encoder located at the motor to detect an angle or direction of rotation of the motor,
wherein when the operating part is rotationally operated in a first direction whereby the operating part is changed from a state where the moving part is bent into a second direction that is a reverse direction relative to the first direction, a direction of rotation of the operating part is detected by the first encoder, as a result of which the operating part-side pulley is disengaged from the first clutch by the controller, allowing the operating part-side pulley to be connected to the second clutch of the motor and the operating part-side pulley connected to the motor to pull the wire.

* * * * *